United States Patent [19]

Blasi et al.

[11] Patent Number: 5,416,006

[45] Date of Patent: May 16, 1995

[54] MODIFICATION OF PLASMINOGEN ACTIVATORS

[76] Inventors: Francesco Blasi, T1glgårdsvej 19A,, DK-2920 Charlottenlund, Denmark; Maria P. Stoppelli, IIa Trav. L. Bianchi, 389; Maria R. Mastronicola, Via Nicolardi, 109,, both of I-80131 Napoli, Italy; Karen G. Welinder, Åmosebakken 14,, DK-2830 Virum, Denmark; Isabel Correas, C. Doctor Esquerdo 140-1, 7c, E-28007 Madrid, Spain

[21] Appl. No.: 603,675

[22] PCT Filed: Apr. 11, 1990

[86] PCT No.: PCT/DK90/00096

§ 371 Date: Dec. 18, 1991

§ 102(e) Date: Dec. 18, 1991

[87] PCT Pub. No.: WO90/12872

PCT Pub. Date: Nov. 1, 1990

[30] Foreign Application Priority Data

Apr. 14, 1989 [DK] Denmark ............... 1822/89

[51] Int. Cl.⁶ .................... C07K 3/12; C12N 5/06; C12N 9/72; C12P 9/00
[52] U.S. Cl. ................... 435/68.1; 435/69.1; 435/70.3; 435/131; 435/215; 530/412
[58] Field of Search ............... 435/70.1, 70.3, 215, 435/803, 226, 69.1, 212, 172.3, 194, 68.1; 424/94.63; 530/417

[56] References Cited

U.S. PATENT DOCUMENTS 5,055,295 10/1991 Welzel ................ 424/94.2

FOREIGN PATENT DOCUMENTS 0190711 4/1989 European Pat. Off. .

OTHER PUBLICATIONS

Yokoigawa, K. et al. *Agric. Biol. Chem.* 48(6):1587–1593 (1984).

Stump, D. C. et al. *J. Biol. Chem.* 261(36):17120–17126 (1986).

Holmberg, L. et al. *Biochimica et Biophysica Acta* 445:212–222 (1976).

Nigg, et al., *Mechanisms of Control of Gene Expression* (1988); 67: 169–177.

Linnala-Kankkunen, et al., *Comp. Biochem. Physiol.* (1988) 90B(1): 91–94.

Martin, P., *Biochimie* (1984); 66(5): 371–384.

Cohen, P., *Chem. Abstracts* (1989); 110: 108255r.

Andreasen, et al., *J. Biol. Chem.* (Jun. 1986); 261(17): 7644–7651.

Andreasen, et al., *FEBS* (Dec. 1986);209(2): 213–218.

Appella, et al., *J. Biol. Chem.* (Apr. 1987); 262(10): 4437–4440.

Cubellis et al., *Proc. Natl. Acad. Sci.-U.S.A.* (Jul. 1989); 86: 4828–4832.

Nolli, et al., *Thrombosis and Haemostasis* (1986); 56(2): 214–218.

Verde, et al., *Proc. Natl. Acad. Sci.-U.S.A.* (Aug. 1984); 81: 4727–4731.

*Primary Examiner*—Robert A. Wax
*Assistant Examiner*—Dian C. Jacobson
*Attorney, Agent, or Firm*—John P. White; Matthew J. Golden

[57] ABSTRACT

Phosphorylated plasminogen activator, such as phosphorylated pro-urokinase (pro-u-PA), which is substantially free from unphosphorylated plasminogen activator, may be obtained by phosphorylating unphosphorylated plasminogen activator with a phosphorylating enzyme or by separating phosphorylated plasminogen activator from a mixture of phosphorylated plasminogen activator and unphosphorylated plasminogen activator. Phosphorylated pro-u-PA, which is substantially free from unphosphorylated pro-u-PA, is converted by plasmin into phosphorylated u-PA. The phosphorylated plasminogen activators such as phosphorylated pro-u-PA, u-PA and t-PA are useful as thrombolytic agents.

17 Claims, 15 Drawing Sheets

MODIFICATION OF PLASMINOGEN ACTIVATORS

The present invention relates to forms of plasminogen activators, their preparation, pharmaceutical compositions containing them, and antibodies specifically recognizing them.

Plasminogen activation (PA) is required intravascularly for digesting fibrin clots, and extravascularly for regulating the interactions between cell surfaces and the protein components of the extracellular matrix and of the basement membrane. The product of the PA reaction, plasmin, can degrade fibrin, proteoglycans, fibronectin, laminin and some collagens; in addition, it is also able to activate latent collagenases. The PA system is composed of the two plasminogen activating enzymes, urokinase (u-PA) and tissue PA (t-PA), and by specific PA inhibitors (PAI-1 and PAI-2). In addition, a specific receptor has been identified for u-PA. While the function of the catalytic moiety of these proteases is better understood, that of the regulatory domains is less clear and only now is information being gathered. For example in u-PA, the growth factor domain is responsible for the binding to the u-PA receptor. In t-PA, the finger domain and the second kringle domain mediate the binding of the enzyme to fibrin.

This system allows the formation of plasmin, both in solution and surface-bound. For the latter, the same cells may have receptors for both plasminogen and plasminogen activators as is the case for the human U937 cells and HT1080 cells. Second, in HT1080 cells, receptor-bound u-PA is able to produce receptor-bound plasmin. Surface plasmin-directed proteolysis appears to have several peculiarities: a) receptor-bound pro-u-PA is activated to two-chain u-PA with a rate that is much faster than in solution; b) surface-bound plasmin is resistant to $\alpha$-2 antiplasmin; and c) receptor-bound u-PA, on the other hand, is active and accessible to inhibition by PAI-1, at least in U937 cells.

u-PA is secreted as a 431 amino acids inactive protein, pro-urokinase (pro-u-PA), which can be bound to surface receptors (u-PAR) and activated by a single proteolytic cleavage. In the malignant A431 cell line, all u-PAR sites are occupied by pro-u-PA ligand produced by the same cells in an autocrine way. Similar results have been reported for a variety of u-PA-producing human tumor cells.

Pro-u-PA is cleaved between amino acid 157 (Lys) and 158 (Ile) to activate the proenzyme. Cleavage results in the formation of the two-chain active u-PA. Although not known in detail, this cleavage is thought to change the secondary and tertiary structure of protease so as to unmask the active site and make it accessible to the substrate (plasminogen) and the inhibitors (PAI-1, PAI-2, protease nexin, $\alpha_2$-macroglobulin, and others). Cleavage of pro-u-PA at the activation site in fact results in a conformational change and in the gain of plasminogen activator activity, both with natural and synthetic substrates.

Half-life of Therapeutically Used Plasminogen Activators

Plasminogen activators (u-PA, t-PA, pro-u-PA, streptokinase and derivatives thereof) are or can be utilized in thromboembolic therapy. One of the problems connected with this therapy is the very high dosage required which is, at least in part, due to the very rapid clearance of these agents. Possible reasons for the short half-life include binding to specific circulating inhibitors, binding to receptors, internalization and degradation of inhibitor-bound and/or receptor-bound plasminogen activator.

The data presented in Examples 8, 9 and 10 show that phosphorylated pro-u-PA is receptor-bound, that binding to receptor is not required for phosphorylation, and that phosphorylated two-chain u-PA shows a dramatic decrease in its sensitivity to PAI-1. It is therefore proposed: firstly, that phosphorylated plasminogen activators may have a longer half-life than non-phosphorylated plasminogen activators since it would not bind PAI-1. Secondly, that fully phosphorylated plasminogen activators could be employed in thromboembolic therapy since, as their non-phosphorylated homologues, they can be activated, e.g. in the case of pro-u-PA to its two-chain active forms (see Example 2). Thirdly, that fully phosphorylated plasminogen activators can be dephosphorylated in situ by existing surface-bound phosphatases (Ballou and Fisher, 1986) or by still-to-be discovered synthetic or natural phosphatases. Thus, phosphorylated proteases would be inactive in the circulation, activatable at the site where they are required, and resistant to the action of inhibitors present in the general circulation.

In its broadest aspect, the present invention provides phosphorylated plasminogen activator which is substantially free from unphosphorylated plasminogen activator. Typically, substantially all of the plasminogen activator molecules have substantially all of their phosphorylatable moieties phosphorylated.

The phosphorylated plasminogen activator according to the invention may be obtained by separating phosphorylated plasminogen activator from a mixture of phosphorylated plasminogen activator and unphosphorylated plasminogen activator, produced by procaryotic or eucaryotic cells. Suitably, the phosphorylated plasminogen activator can be obtained by:

(i) culturing a human cell line which produces a plasminogen activator;
(ii) isolating the plasminogen activator thus produced; and
(iii) separating the phosphorylated plasminogen activator from the unphosphorylated plasminogen activator.

The phosphorylated plasminogen activator is typically separated in step (iii) by chromatography, for example by $Fe^{3+}$-chelating chromatography. A cross-linked dextran may be employed. For example, separation may be achieved by column chromatography. Sepharose may be used. Typically, plasminogen activator is provided in a solution of a pH of about 3. The pH may be adjusted using acetic acid, for example 0.1M acetic acid. The solution is loaded onto a column. The column is eluted using a potassium phosphate buffer. The buffer pH is typically about 8.0. The eluate of phosphorylated plasminogen activator free of unphosphorylated plasminogen activator is collected.

Alternatively, phosphorylated plasminogen activator may be obtained substantially free from unphosphorylated plasminogen activator by phosphorylating unphosphorylated plasminogen activator with a phosphorylating enzyme. A mixture of phosphorylated and unphosphorylated plasminogen activator can be treated with the phosphorylating enzyme.

The phosphorylated plasminogen activators according to the invention are useful as therapeutic agents in cases of venous and arterial thrombotic episodes, such as heart infarction, deep vein thrombosis and strokes. It is contemplated that none of the phosphorylated plasminogen activators bind the plasminogen activator inhibitors. The phosphorylated plasminogen activators can therefore have a longer half life because of their resistance to the action of inhibitors present in the general circulation.

An effective amount of phosphorylated plasminogen activator according to the invention is administered to a patient in need of it. Administration to a mammal, preferably a human being, may be performed parenterally and preferably intravenously. Typically a dose of from 4 to 40 mg, for example from 5 to 10 mg, of the phosphorylated plasminogen activator is given parenterally.

The invention also relates to pharmaceutical compositions comprising the phosphorylated plasminogen activator according to the invention and a pharmaceutically acceptable carrier or diluent. The phosphorylated plasminogen activator may therefore be presented in a sterile, pyrogen-free aqueous solution, or in any other appropriate fashion.

Thus, very important embodiments of the invention are constituted by the treatment of u-PA, pro-u-PA, or t-PA with a phosphorylating enzyme, in particular a protein kinase, to phosphorylate the u-PA, pro-u-PA, or t-PA. The phosphorylated substance may be used in the same manner as u-PA, pro-u-PA and t-PA are used in the treatment of e.g. thromboembolic diseases and other diseases as mentioned above. As the half-life of the administered (e.g. injected) substance is increased in accordance with the principles explained above as the inactivation of the substance by inhibitors (such as PAI-1 or PAI-2) is prevented by the phosphorylation, the dosage might be reduced accordingly.

As is explained in detail in the examples, it has been found that pro-u-PA is phosphorylated. In particular, it has been found that phosphorylation occurs on specific serine residues. Phosphorylated pro-u-PA substantially free from unphosphorylated pro-u-PA has been obtained and cleaved by plasmin to form phosphorylated u-PA. It has also been found that, advantageously, the phosphorylated u-PA fails to bind to the inhibitor PAI-1.

Accordingly, the present invention provides phosphorylated pro-u-PA which is substantially free from unphosphorylated pro-u-PA. Typically, substantially all of the pro-u-PA molecules have substantially all of their phosphorylatable moieties phosphorylated.

Treatment of the phosphorylated pro-u-PA with plasmin yields phosphorylated u-PA which is substantially free from unphosphorylated u-PA. The phosphorylated u-PA is resistant to PAI-1. The phosphorylated pro-u-PA is therefore phosphorylated on an amino acid residue which ensures that the phosphorylated u-PA resulting from treatment of the phosphorylated pro-u-PA with plasmin is insensitive to PAI-1.

It has in fact been ascertained that fully phosphorylated pro-u-PA is phosphorylated at two sites. Each site is a serine residue. One site is the serine residue at amino acid position 303. The other site is a serine residue at position 138 and/or 139. The numbers of the amino acids are according to Verde et al., 1984. The molecular weight of the phosphorylated pro-u-PA is 47 kD, as determined by electrophoresis on an agarose gel. The phosphorylated pro-u-PA does not bind to PAI-1.

The phosphorylated pro-u-PA according to the invention may be obtained by separating phosphorylated pro-u-PA from a mixture of phosphorylated pro-u-PA and unphosphorylated pro-u-PA. pro-u-PA produced by procaryotic or eucaryotic cells, for example produced in bacteria, yeasts or mammalian cells, is in fact a mixture of phosphorylated and unphosphorylated pro-u-PA. Suitably, the phosphorylated pro-u-PA can be obtained by:
  (i) culturing a human cell line which produces pro-u-PA, for example the A431 or HT1080 cell line;
  (ii) isolating the pro-u-PA thus produced; and
  (iii) separating the phosphorylated pro-u-PA from the unphosphorylated pro-u-PA.

The phosphorylated pro-u-PA is typically separated in step (iii) by chromatography, for example by $Fe^{3+}$-chelating chromatography. A cross-linked dextran may be employed. For example, separation may be achieved by column chromatography. Sepharose may be used. Typically, pro-u-PA is provided in a solution of a pH of about 3. The pH may be adjusted using acetic acid, for example 0.1M acetic acid. The solution is loaded onto a column. The column is eluted using a potassium phosphate buffer. The buffer pH is typically about 8.0. The eluate of phosphorylated pro-u-PA free of unphosphorylated pro-u-PA is collected.

Alternatively, phosphorylated pro-u-PA may be obtained substantially free from unphosphorylated pro-u-PA by phosphorylating unphosphorylated pro-u-PA with a phosphorylating enzyme. A mixture of phosphorylated and unphosphorylated pro-u-PA can be treated with the phosphorylating enzyme. Casein kinase II may be employed to phosphorylate the phosphorylatable site composed of the serine residue(s) at position 138 and/or 139.

The phosphorylated pro-u-PA and u-PA according to the invention are useful as therapeutic agents in cases of venous and arterial thrombotic episodes, such as heart infarction, deep vein thrombosis and strokes. The phosphorylated pro-u-PA can be cleaved to yield phosphorylated two-chain u-PA. The phosphorylated two-chain u-PA or, for that matter, the phosphorylated pro-u-PA cannot properly bind the inhibitor PAI-1. The phosphorylated plasminogen activators can therefore have a longer half life because of their resistance to the action of inhibitors present in the general circulation.

An effective amount of phosphorylated pro-u-PA or u-PA according to the invention is administered to a patient in need of it. Administration to a mammal, preferably a human being, may be performed parenterally and preferably intravenously. Typically a dose of from 4 to 40 mg, for example from 5 to 10 mg, of the phosphorylated pro-u-PA or u-PA is given parenterally.

The invention also relates to pharmaceutical compositions comprising the phosphorylated pro-u-PA or u-PA according to the invention and a pharmaceutically acceptable carrier or diluent. The phosphorylated pro-u-PA or u-PA may therefore be presented in a sterile, pyrogen-free aqueous solution, or in any other appropriate fashion.

The tissue-type plasminogen activator, t-PA, also contains phosphorylatable residues in a position analogous to serine 303 residue of pro-u-PA. It is on this background that it is contemplated that phosphorylated t-PA, in particularly phosphorylated t-PA substantially free from unphosphorylated t-PA, can be obtained by the same methods as described for pro-u-PA and u-PA, and that such a product can be used for the same purposes.

It is often desirable that the plasminogen activator is substantially 100% phosphorylated, i.e. that substantially all of the protease molecules have substantially all of their phosphorylatable moieties phosphorylated. However, also plasminogen activators such as pro-u-PA, u-PA or tPA with a lower degree of phosphorylation such as in the range of 70–100%, such as 80–100%, e.g. 90–100% or 95–100%, are interesting. The present invention thus makes it possible to obtain plasminogen activator such as pro-u-PA with a higher degree of phosphorylation than the naturally occurring product, e.g. 70%, 80% or 90%, e.g. by increasing the degree of phosphorylation by phosphorylation with a phosphorylating enzyme.

In a further aspect, the present invention relates to antibodies specifically recognizing phosphorylated plasminogen activator, in particular phosphorylated pro-u-PA or phosphorylated u-PA. Such antibodies may be useful for recognizing cancer cells which produce u-PA phosphorylated to a higher degree than normal cells, cf. Example 1 below. Such antibodies may be produced by a method which comprises administering in an immunogenic form at least a part of the phosphorylated protease to obtain cells producing antibodies reactive with said phosphorylated protease and isolating the antibody containing material from the organism or the cells. The methods of producing antibodies will be explained further below.

The antibody is preferably a monospecific antibody. The monospecific antibody may be prepared by injecting a suitable animal with a substantially pure preparation of the phosphorylated protease followed by one or more booster injections at suitable intervals (e.g. one or two weeks to a month) up to four or five months before the first bleeding. The established immunization schedule is continued, and the animals are bled about one week after each booster immunization, and antibody is isolated from the serum in a suitable manner (cf. e.g. Harboe and Ingild, 1973).

For purposes not requiring a high assay specificity, the antibody may be a polyclonal antibody. Polyclonal antibodies may be obtained, e.g. as described in Harboe and Ingild, see above. More specifically, when polyclonal antibodies are to be obtained, the phosphorylated protease is, preferably after addition of a suitable adjuvant, such as Freund's incomplete or complete adjuvant, injected into an animal. When the immunogens are human phosphorylated protease, the animals may be rabbits. The animals are bled regularly, for instance at weekly intervals, and the blood obtained is separated into an antibody containing serum fraction, and optionally said fraction is subjected to further conventional procedures for antibody purification, and/or procedures involving use of purified phosphorylated proteases.

In another preferred embodiment, monoclonal antibodies are obtained. The monoclonal antibody may be raised against or directed substantially against an essential component of phosphorylated proteases, i.e. an epitope. The monoclonal antibody may be produced by conventional techniques (e.g. as described by Köhler and Milstein, 1975), e.g. by use of a hybridoma cell line, or by clones or subclones thereof or by cells carrying genetic information from the hybridoma cell line coding for said monoclonal antibody. The monoclonal antibody may be produced by fusing cells producing the monoclonal antibody with cells of a suitable cell line, and selecting and cloning the resulting hybridoma cells producing said monoclonal antibody. Alternatively, the monoclonal antibody may be produced by immortalizing an unfused cell line producing said monoclonal antibody, subsequently growing the cells in a suitable medium to produce said antibody, and harvesting the monoclonal antibody from the growth medium.

The immunized animal used for the preparation of antibodies of the invention is preferably selected from the group consisting of rabbit, monkey, sheep, goat, mouse, rat, pig, horse and guinea pigs. The cells producing the antibodies of the invention may be spleen cells or lymph cells, e.g. peripheral lymphocytes.

When hybridoma cells are used in the production of antibodies of the invention, these may be grown in vitro or in a body cavity of an animal. The antibody-producing cell is injected into an animal such as a mouse resulting in the formation of an ascites tumour which releases high concentrations of the antibody in the ascites of the animal. Although the animals will also produce normal antibodies, these will only amount to a minor percentage of the monoclonal antibodies which may be purified from ascites by standard purification procedures such as centrifugation, filtration, precipitation, chromatography or a combination thereof.

An example of a suitable manner in which the monoclonal antibody may be produced is as a result of fusing spleen cells from immunized mice (such as Balb/c mice) with myeloma cells using conventional techniques (e.g. as described by R. Dalchau et al., 1980). The fusions obtained are screened by conventional techniques such as binding assays employing phosphorylated proteases.

The antibodies specifically recognizing phosphorylated pro-u-PA or phosphorylated u-PA can be used to determine their presence in a sample. A sample suspected of containing phosphorylated pro-u-PA or phosphorylated u-PA is contacted with the antibody, and the presence or absence of an immune complex between the phosphorylated pro-u-PA or u-PA and the antibody is determined. Any convenient procedure may be adapted for this purpose.

A diagnostic agent may be provided which comprises an antibody as defined above, preferably a monoclonal antibody, and means for determining whether in use the antibody has formed an immune complex with a phosphorylated plasminogen activator such as t-PA, pro-u-PA or u-PA. The agent may be provided as a test kit comprising a phosphorylated protease in a container. The diagnostic agent may be used in the diagnosis of diseases related to phosphorylated proteases.

The administration of the various above-mentioned phosphorylated plasminogen activators to a mammal, preferably a human being, may be performed parenterally, in particular intravenously, in analogy with the administration method presently used for u-PA, pro-u-PA and t-PA.

The following Examples illustrate the invention. In the figures:

FIGS. 1A–1B shows that the pro-u-PA secreted by A431 cells is phosphorylated. Immunoprecipitation of $^{35}$S- (FIG. 1A) and $^{32}$P-labelled (FIG. 1B) A431 and HT-1080 cell medium using 5B4 monoclonal antibody coupled to agarose (lane Ab). In lane C, medium was precipitated with glycine-blocked agarose. Lane M: molecular weight markers.

FIG. 2 shows the limited digestion of the immunoprecipitated $^{32}$P-pro-u-PA with plasmin. Duplicate immunoprecipitates from the labelled medium are treated (lanes 2, 3) or not (lanes 0, 1) with plasmin. Lane C:

control immunoprecipitate in which labelled medium was incubated with glycine-blocked agarose.

FIG. 3 shows the results of the determination of the phosphorylated amino acid in $^{32}$P-pro-u-PA. The immunoprecipitated $^{32}$P medium was subjected to acid hydrolysis and analyzed by high voltage electrophoresis on thin layer plates in the presence of unlabelled phosphoamino acids markers.

FIG. 4 shows that exogenous two-chain u-PA is not phosphorylated in A431 cell medium. Immunoprecipitation of the $^{32}$P-labelled medium of A431 cells to which none (lane —) or 7.5 μg of unlabelled two-chain u-PA (lane +) had been added during the labelling period. Lane C: control immunoprecipitated Lane M: molecular weight markers.

FIG. 5 shows that intracellular pro-u-PA is phosphorylated. Two sets of A431 cells were labelled with either $^{35}$S-methionine (panel A) or $^{32}$P-orthophosphate (panel B), acid-washed, and lysed. Lanes A, C: control immunoprecipitates. Lanes B, D: immunoprecipitation with antibody 5B4. Lane M: molecular weight markers.

FIG. 6 shows the results of a pulse-chase experiment of pro-u-PA phosphorylation and secretion in PMA-treated A431 cells.

Left panel: PMA-treated A431 cells were labelled for 7 hours with $^{32}$P-orthophosphate, acid washed and the labelling medium removed and substituted with normal DMEM. The chase period lasted 16 hours. Lane 1: molecular weight markers. Lane 2: immunoprecipitation from the 7 hours labelled medium. Lane 3: immunoprecipitation of the acid-washed cell lysate at the end of the 7 hours labelling period. Lane 4: immunoprecipitation from the medium after 16 hours of chase. Lane 5: immunoprecipitation of the acid-washed cell lysate after 16 hours chase period.

Right panel: A431 cells were labelled for 18 hours with $^{32}$P-orthophosphate, the labelling medium substituted with normal DMEM and chased with medium containing unlabelled phosphate for 3, 5, 8 and 11 hours. At each time point, the medium was immunoprecipitated. The lane marked "pre-chase" shows immunoprecipitation of the medium at the end of the 18 hours labelling period.

FIG. 7 shows that receptor-bound pro-u-PA is phosphorylated in A431 cells as shown by the specific immunoprecipitation of $^{32}$P-pro-u-PA from the acid wash of labelled A431 cells. Lane 1: control immunoprecipitation; lane 2: immunoprecipitation with monoclonal antibody 5B4.

FIG. 8 shows that receptor binding is not required for pro-u-PA phosphorylation. Immunoprecipitation of the conditioned medium and of the acid wash of A431 cells labelled with $^{35}$S (lanes 1 to 3) and $^{32}$P (lanes 4 to 7). Effect of 0.1 mM synthetic peptide [u-PA(12–32)ala19] that competes for the binding to the u-PA receptor. Lanes 1a, 1b: immunoprecipitation of the acid wash of $^{35}$S cells incubated in the presence and absence of peptide, respectively. Lanes 2, 4 and 5: immunoprecipitates of conditioned media from cells incubated in the absence of peptide. Lanes 3, 6 and 7: immunoprecipitates of conditioned media from cells incubated in the presence of peptide.

FIG. 9 shows the binding of $^{35}$S- and $^{32}$P-labelled, immunoprecipitated, plasmin-treated pro-u-PA from A431 conditioned media to PAI-1.
Lane M: molecular weight markers;
lanes 1, 4: untreated $^{32}$P and $^{35}$S labelled pro-u-PA from immunoprecipitated A431 medium;
lanes 2, 5: same, but after plasmin treatment of pro-u-PA;
lanes 3, 6: same as in lanes 2, 5, but after binding to PAI-1 (at a PAI-1 to pro-u-PA ratio of 12.5).

Figure 13A:
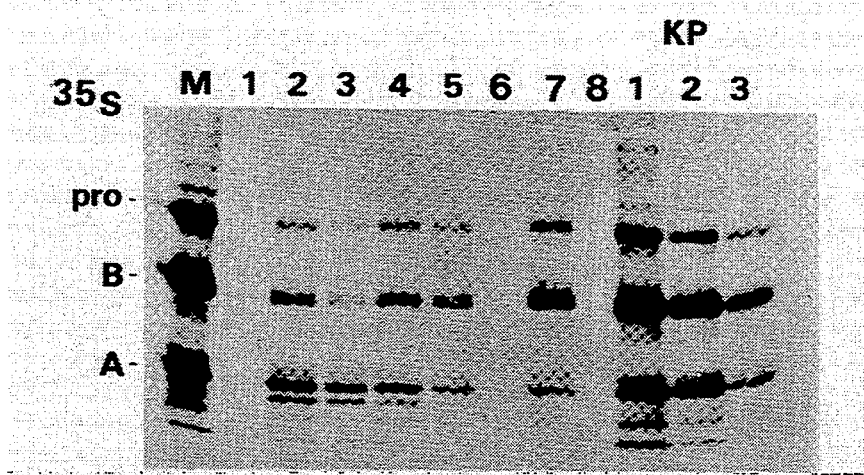
Figure 13B:
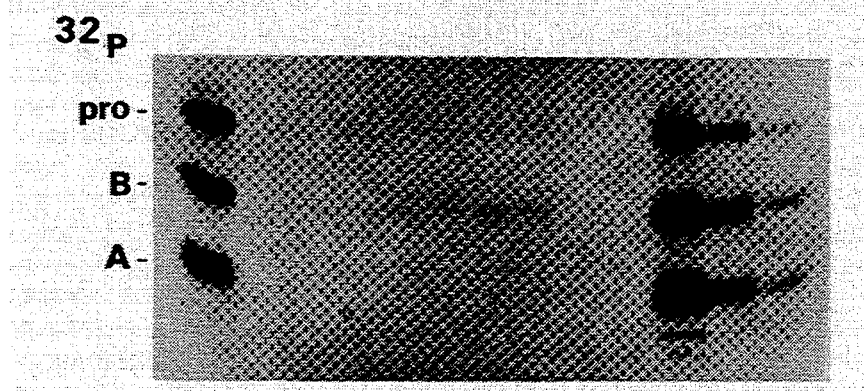

FIG. 13 shows the results of SDS-polyacrylamide (12.5%) gel analysis of the fractions of the $Fe^{3+}$-Sepharose batchwise elution of $^{35}$S (TOP) and $^{32}$P (BOTTOM). Gels are run under reduced conditions.
Lane M: molecular weight markers
Lane 1: supernatant after the incubation
Lane 2: elution in 0.5M sodium acetate pH 3
Lane 3: same, pH 4
Lane 4: same, pH 5
Lane 5: same, pH 5.5
Lane 6: same, pH 6.5
Lane 7: elution in 1% ammonium acetate pH 7.0
Lane 8: same, pH 8.0
Lane KP-1: elution with potassium phosphate, 0.5M NaCl pH 8.0, fraction 1
Lane KP-2: same, fraction 2
Lane KP-3: elution in 0.1M EDTA, 0.05M Tris-HCl pH 7.5, 0.5M Nacl.

The symbol pro indicates the migration of single-chain pro-u-PA. The symbols B and A indicate the migration of the A and B chains of two-chain u-PA.

Figure 14A:
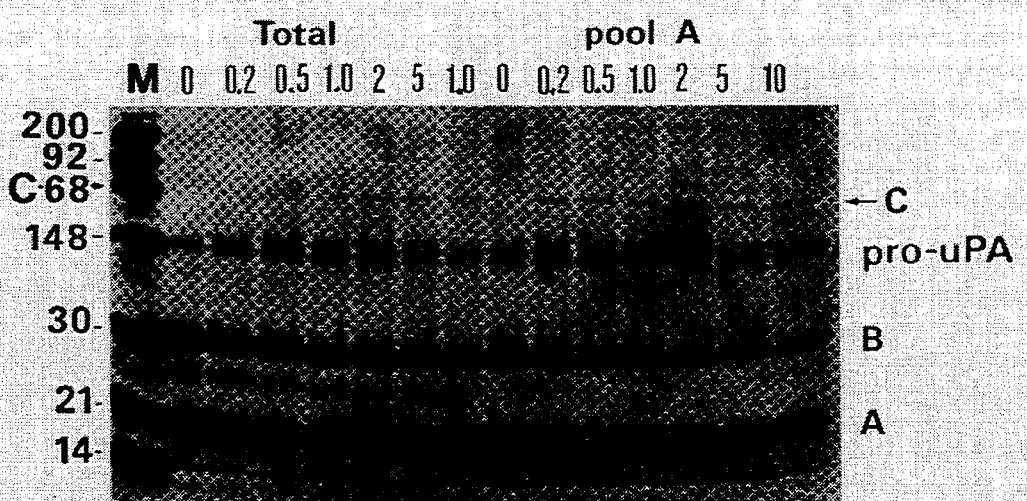
Figure 14B:
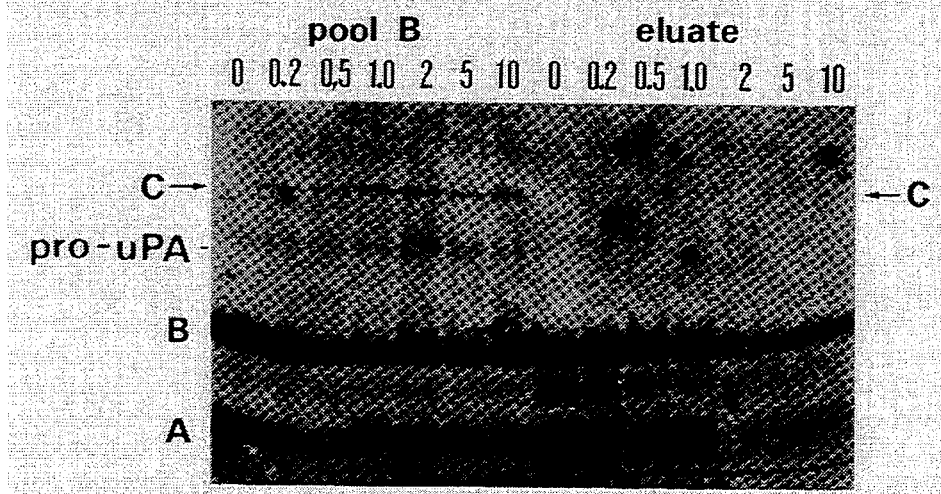

FIG. 14 shows the results of assaying the eluates from a $^{35}$S-pro-u-PA $Fe^{3+}$-chelating Sepharose column for PAI-1 sensitivity.

EXAMPLES

Materials and Reagents

Reagents

Bovine serum albumin (BSA), 3-trimethylsilyl-1-propanesulfonic acid (DSS), aprotinin, leupeptin, benzamidine, phenylmethylsulfonyl fluoride (PMSF), sodium orthovanadate and plasmin were from Sigma. Agarose was from BRL. Dulbecco's modified Eagle's medium (DMEM), methionine-free DMEM, phosphate-free DMEM, fetal bovine serum (FBS), dialyzed fetal bovine serum (dFBS) and glutamine were from Gibco.

$^{35}$S-methionine, $^{32}$P-orthophosphate and $^{14}$C molecular weight markers (high range) were from Amersham. Affigel used for protein coupling, acrylamide, bis-acrylamide, Temed, ammonium persulphate and bromophenol blue were from Biorad. Enlightning was from NEN.

The 5B4 monoclonal antibody was obtained from Lepetit S.p.A. laboratories, Milan, Italy (Nolli et al., 1986). The synthetic peptide [u-PA(12–32)ala19] was kindly provided by Ettore Appella (N.I.H.) (Appella et al., 1987).

Cell Lines

The A431 cell line (Fabricant et al., 1977; Stoppelli et al., 1986) was derived from an 85-year-old female carrying an epidermoid carcinoma of vulva. It was obtained from I. Pastan, NIH, Bethesda, Md., USA. The HT1080 cell line (Andreasen, et al., 1986) was derived from a fibrosarcoma arising adjacent to the acetabulum of a 35-year-old Caucasian male. It was obtained from K. Danø's laboratory, Copenhagen, Denmark. Both cell lines grow adherent to the tissue culture dish in DMEM supplemented with 10% FBS in a 10% $CO_2$ atmosphere.

Example 1

In Vivo Phosphorylation of pro-u-PA

In order to determine whether pro-u-PA secreted by a human cell line carries a phosphate group, A431 cells were labelled with $^{32}$P-orthophosphate according to the following procedure:

Method

Cell Labelling

Day 1: A431 or HT1080 cells were seeded at a density of $1.5 \times 10^6$ cells in a 10 cm dish in 10 ml of DMEM+10% FBS and grown for 24 hours.

Day 2: The medium was aspirated from the cells and substituted with 5 ml of methionine-free or phosphate-free DMEM+5% dFBS. After 6 hours, this medium is further substituted either with 2 ml of methionine-free medium containing 400 μCi of $^{35}$S-methionine or with 2 ml of phosphate-free medium containing 600 μCi of $^{32}$P-orthophosphate. The labelling period was 18 hours.

Day 3: The $^{35}$S and the $^{32}$P conditioned culture media were collected with a Pasteur pipette and centrifuged at 1500 rpm for 10 minutes at room temperature in a Heraeus Sepatech Labofuge T to remove dead cells and cell debris. At the end of the centrifugation, the supernatants were collected and used as a starting material for the immunoprecipitation procedure which was as follows:

Immunoprecipitation

Step 1: 0.3 ml of $^{35}$S and 1 ml of $^{32}$P labelled media were used for each sample and supplemented with 0.1 and 0.3 ml, respectively, of potassium phosphate buffer (PPB; 0.22M $K_2HPO_4$, pH 7.0, 0.2M NaCl, 0.4% Triton X-100) at room temperature.

Step 2: The actual immunoprecipitation (Stoppelli et al., 1986) was performed using the 5B4 monoclonal antibody coupled to Affigel and kept in a 1:1 suspension in 4-fold diluted PPB. Control samples were incubated with glycine-blocked Affigel kept under the same conditions. The volume of 5B4 used was 1/25 of the total reaction volume; the incubation was performed for 1 hour at room temperature with gentle shaking.

Step 3: The reaction tubes were centrifuged in a microfuge at 10,000×g for 3 minutes and the supernatant discarded. The pellets were resuspended in 1 ml of 4-fold diluted PPB and centrifuged for 3 minutes in an Eppendorf microfuge. The same procedure was repeated 3 more times.

Step 4: The pellets were then resuspended in 0.4 ml of elution buffer (EB: 0.1M glycine-HCl, pH 2.5, 0.5M NaCl, 0.1% Triton X-100) and incubated for 15 minutes at room temperature with gentle shaking. The samples were centrifuged as described in step 3 and the supernatants recovered.

Step 5: The supernatants were precipitated with trichloroacetic acid (final concentration=20%) with cytochrome C (70 μg) as a carrier; they were incubated on ice for 20 minutes and centrifuged as described in step 3. The pellets were washed with 1 ml of diethyl ether, centrifuged, further washed with 1 ml of acetone, centrifuged, and air-dried.

Step 6: The pellets were resuspended in 50 μl of Laemmli buffer (see Laemmli, 1970) (0.14M Tris, pH 6.8, 22.4% glycerol, 6% SDS) and loaded on a 12.5% SDS-PAGE. 5 μl of prestained $^{14C}$ molecular weight markers (high range) were also subjected to the same procedure and loaded on the same gel. Electrophoresis was carried out in 12% polyacrylamide as described by Laemmli, 1970.

Gels containing $^{32}$P samples were directly dried under vacuum for two hours in a Biorad gel dryer. When containing $^{35}$S samples, they were fixed in 25% methanol, 10% acetic acid, embedded in Enlightning (NEN) and dried. The dried gel was then exposed in an autoradiographic cassette with enlightning plus screens (Dupont) using Kodak X-OMAT films.

Results

Figure 1A:
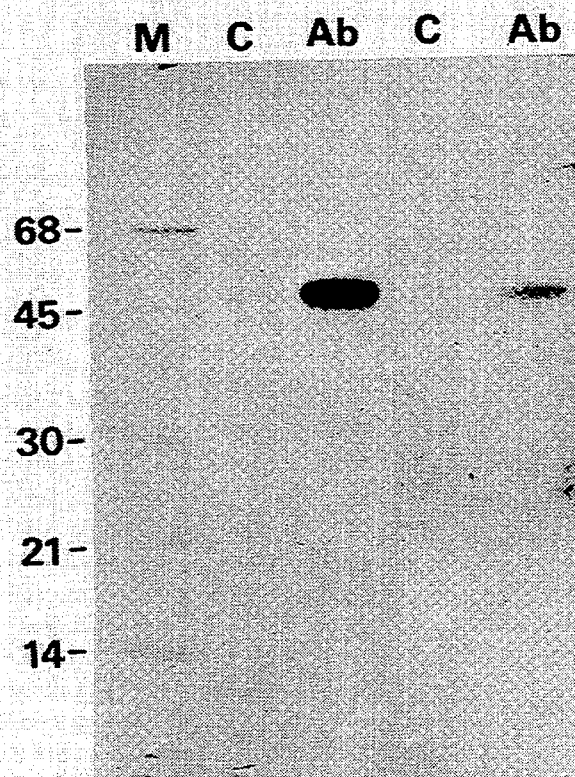
Figure 1B:
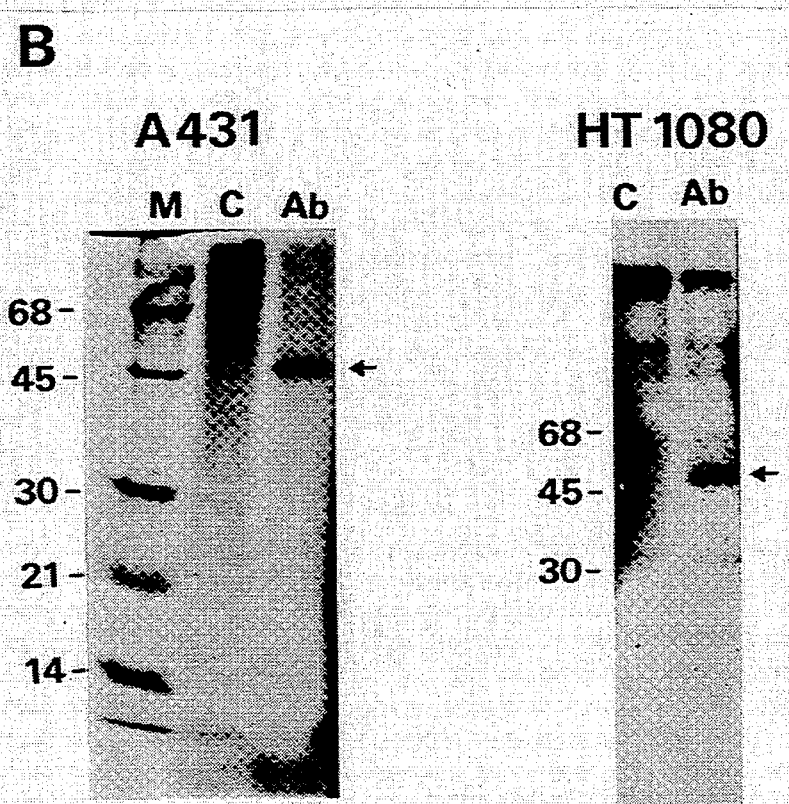

A typical experiment shows a $^{35}$S or $^{32}$P labelled protein of the size of pro-u-PA (47 kilodaltons) which appears when the antibody 5B4 is used. In contrast, lanes resulting from glycine-blocked agarose incubations (control of immunoprecipitation) do not show any band (FIG. 1). The data presented in FIG. 1 refer to A431 cells and HT1080 cells; identical results have been obtained. Therefore, in at least two different cell lines, biosynthetic pro-u-PA is phosphorylated.

Example 2

Determination of the Minimum Number of Phosphorylation Sites on pro-u-PA

Method

It is known that the serine protease plasmin cuts the single chain 47 Kd pro-u-PA at a specific site, giving rise to a molecule with two chains (30 Kd and 17 Kd) (Stoppelli et al., 1986); the molecule retains the enzymatic properties. Chain A (17 Kd) contains regulatory domains; chain B has catalytic domains (Stoppelli et al., 1985; Stoppelli et al., 1986).

This property was used to investigate whether the 47 Kd band resulting from Example 1 is indeed pro-u-PA; therefore, an A431 cell labelling was performed with $^{32}$P-orthophosphate under the same conditions as described in Example 1, followed by immunoprecipitation until step 6.

The pellets resulting from the TCA precipitation were then resuspended in 30 μl of Tris-HCl, pH 6, either in the presence or in the absence of plasmin (concentration of 175 μg/ml); the samples were then incubated at 37° C. for 30 minutes. At the end of the incubation, 30 μl of 2× Laemmli buffer (see Example 1) were added, the sample boiled and loaded onto an SDS-PAGE as described in Example 1.

Results

Figure 2:
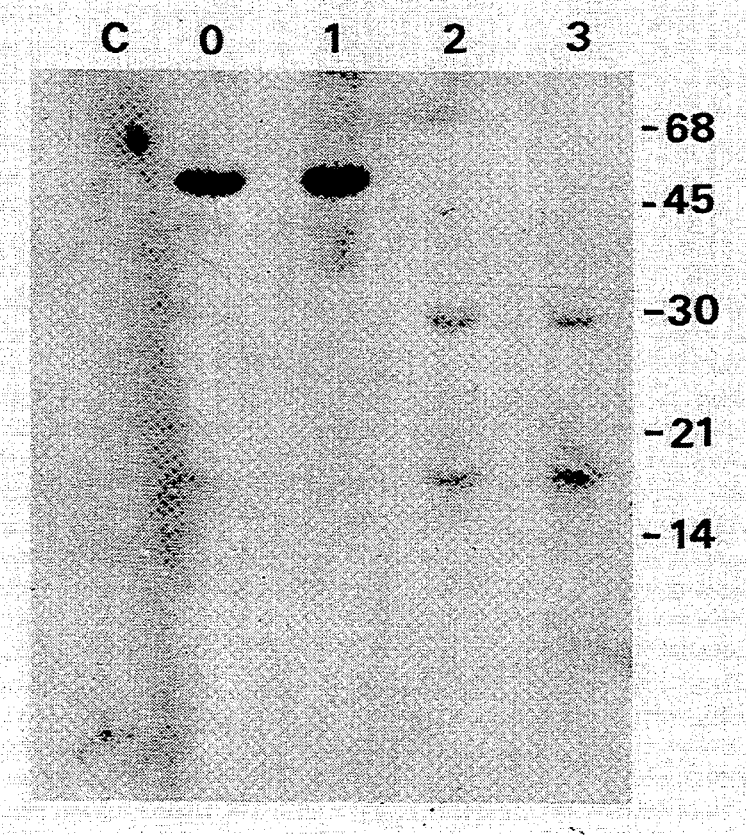

As expected from the cleavage of pro-u-PA by plasmin, which releases two chains of different sizes (17 Kd and 30 Kd, respectively), the incubation of immunoprecipitated $^{32}$P labelled A431-conditioned medium generates two bands of 17 Kd and 30 Kd as opposed to the single 47 Kd band from the control samples (see FIG. 2). Therefore, each of the two chains must contain at least one phosphorylation site. Thus, phosphorylated pro-u-PA has a minimum of two phosphorylation sites.

Example 3

Determination of the Phosphorylated Amino Acid

Phosphorylated proteins may carry the phosphate group covalently bound to serine, threonine or tyrosine; one way to determine which amino acid is involved is to perform a total hydrolysis of the protein, separate and identify the phosphoamino acid.

Method

Cell Labelling and Isolation of Phosphorylated pro-u-PA

Three 10 cm dishes of A431 cells were labelled with $^{32}P$ and the medium was immunoprecipitated as described in Example 1. The SDS-PAGE (see Example 1) was performed using $^{32}P$ immunoprecipitate control of the experiment. Prestained $^{14}C$ molecular weight markers assisted in localizing the region of the gel which contained the labelled pro-u-PA.

Step 1: A slice from the acrylamide gel was excised, corresponding to the pro-u-PA band.

Step 2: The gel slice was boiled in 1 ml of 1% SDS for 15 minutes, homogenized by using an Ultraturrax homogenizer and centrifuged at 4500 rpm for 15 minutes.

Step 3: The supernatant was collected, supplemented with 5 volumes of cold acetone and 50 μg of BSA as a carrier, and incubated at −15° C. for 30 minutes.

Acid Hydrolysis

Step 1: The samples were centrifuged at 4500 rpm for 15 minutes. The protein pellet was washed with 1:1 vol. of ether-ethanol and finally suspended in 1 ml of 6N HCl.

Step 2: The samples were hydrolyzed at 110° C. for 90 minutes and then diluted with water and lyophilized overnight.

Phosphoamino Acid Separation

Step 1: The dried samples were taken up in 20 μl of water containing 2 mg/ml each of cold phosphoserine, phosphothreonine and phosphotyrosine and subjected to one dimension thin layer electrophoresis at 1000 Volts and 4° C. on Macherey-Nagel 100 μm thin layer plates using acetic acid/pyridine/water (50:5:945) at pH 2.5 for 1 hour.

Step 2: After the run, the cellulose plates were dried, stained with ninhydrin and exposed to Kodak X-OMAT X-ray film to detect the $^{32}P$ phosphorylated amino acids.

Results

Figure 3:
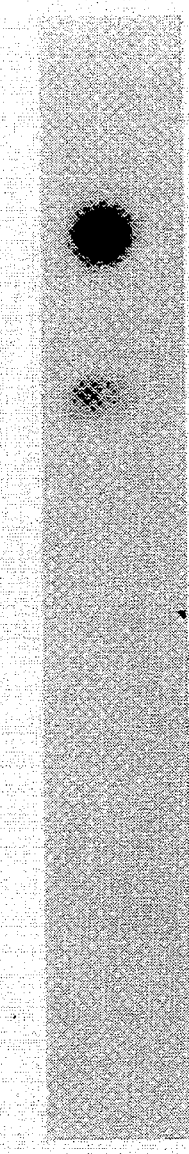

In addition to free phosphate, the only labelled component from the hydrolysis of pro-u-PA that could be detected was a spot which migrated with the phosphoserine unlabelled marker (see FIG. 3). Such a spot did not appear in control samples where a negative control of the immunoprecipitation (glycine-blocked agarose sample; see Example 1) was subjected to the same procedure (not shown).

Example 4

Determination of the Cellular Site of Phosphorylation of pro-u-PA

To exclude the possibility that the pro-u-PA phosphorylation may be an artefact occurring in the cell culture medium during the labelling period, the following experiment was carried out: Two-chain urokinase was added to the cells during the labelling period to test whether it would become phosphorylated.

Method

Step 1: Two 10 cm tissue culture dishes of A431 cells were starved and labelled with $^{32}P$-orthophosphate as described in Example 1. The medium from one of the two dishes was supplemented with 7.5 μg of cold urokinase from the beginning to the end of the labelling period. The other dish was the control of the experiment.

Step 2: At the end of the incubation, 1 ml aliquots of conditioned medium were taken from the dishes and subjected to the immunoprecipitation procedure described in Example 1. Samples were analyzed in duplicate.

Step 3: An SDS-PAGE electrophoresis under reducing conditions followed by autoradiography as described in Example 1 made it possible to visualize the result of the experiment.

Results

Figure 4:
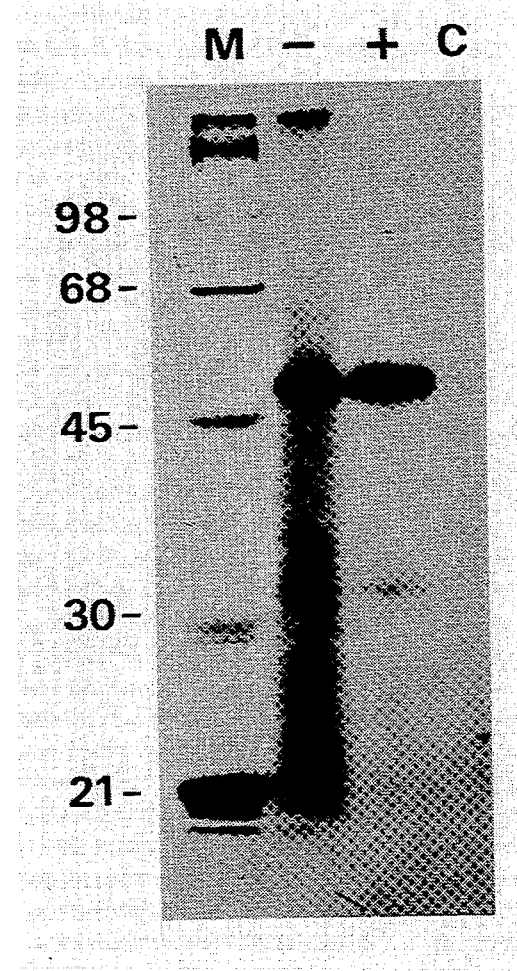

If the phosphorylation may occur in the cell culture medium after pro-u-PA has been secreted, it would be expected that exogenously added urokinase can be phosphorylated as well. In contrast, the gel electrophoresis results show that in both cases, a single 47 Kd band (pro-u-PA) is present which is not accompanied by the 30 Kd and 17 Kd bands which would indicate labelling of two-chain urokinase, even when unlabelled two-chain urinary urokinase is present in the incubation medium (FIG. 4). Therefore, it was concluded that, at least under the present conditions, no secreted or surface-associated factors can account for the phosphorylation observed in Example 1.

Example 5

Intracellular Phosphorylation of pro-u-PA

The results reported in Example 4 suggest that pro-u-PA may be phosphorylated before being secreted. Two different experiments were designed to test this point.

Method

Step 1: The A431 cells labelled and acid washed (see Example 8) were lysed and tested by immunoprecipitation. After the acid wash, the cells were washed two times with phosphate buffered saline, scraped with a rubber policeman, collected in one tube and centrifuged at 1500 rpm for 5 minutes.

Step 2: The supernatant was discarded and the pellet was resuspended in 2 ml of lysis buffer (20 mM Hepes, pH 7.5, 1% Triton X-100, 10% glycerol). The cells were vortexed for 30 seconds and centrifuged in a microfuge at 10,000 rpm and 4° C. for 30 minutes.

Step 3: The supernatant was subjected to the immunoprecipitation and SDS-PAGE procedure as described in Example 1.

Results

Figure 5:
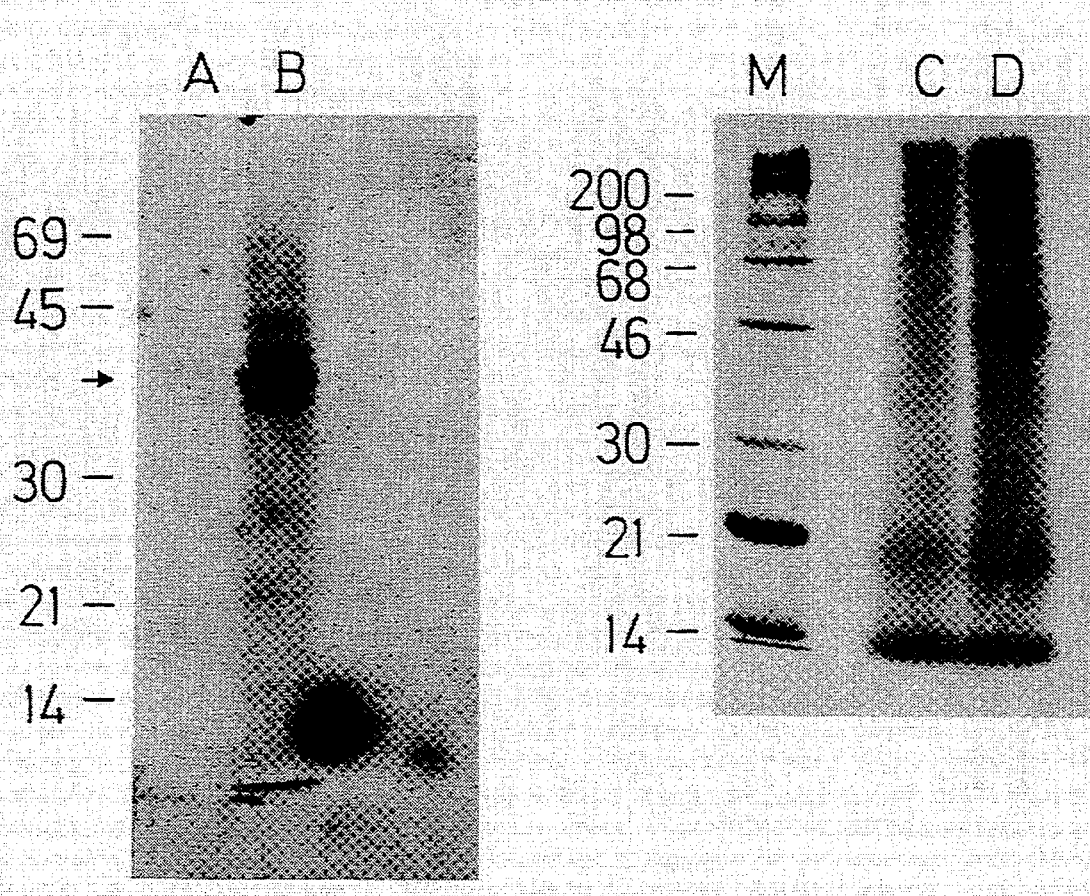

A band was observed corresponding to the pro-u-PA molecular weight (47 Kd) which does not appear in the negative control (see FIG. 5). Thus, labelled pro-u-PA is present in acid-washed A431 cell lysate, that is in the interior of the cell.

Example 6

Pulse-Chase Labelling of Pro-u-PA

Method

Step 1: Four 10 cm dishes of A431 cells were starved overnight and labelled with $^{32}P$-orthophosphate or $^{35}S$-methionine. Phorbol myristate acetate (PMA) was present at a concentration of 50 ng/ml for 7 hours to increase the pro-u-PA output of A431 cells (Stoppelli et al., 1986a).

Step 2: The cells were washed twice with phosphate-free and serum-free DMEM and subjected to acid wash as described in Example 5.

Step 3: Two of the dishes were supplemented with lysis buffer as described in Example 5 and the resulting lysates were frozen. 2 ml of serum-free DMEM (this time containing phosphate) supplemented with 50 ng/ml PMA were added to each of the remaining two dishes which were then incubated for 16 hours at 37° C. and 10% $CO_2$.

Step 4: Plates 3 and 4 were washed again with acid buffer and lysed (see step 3).

Step 5: All lysates and media of the experiment were immunoprecipitated and subjected to SDS-PAGE (see Examples 1 and 5).

Results

Figure 6:
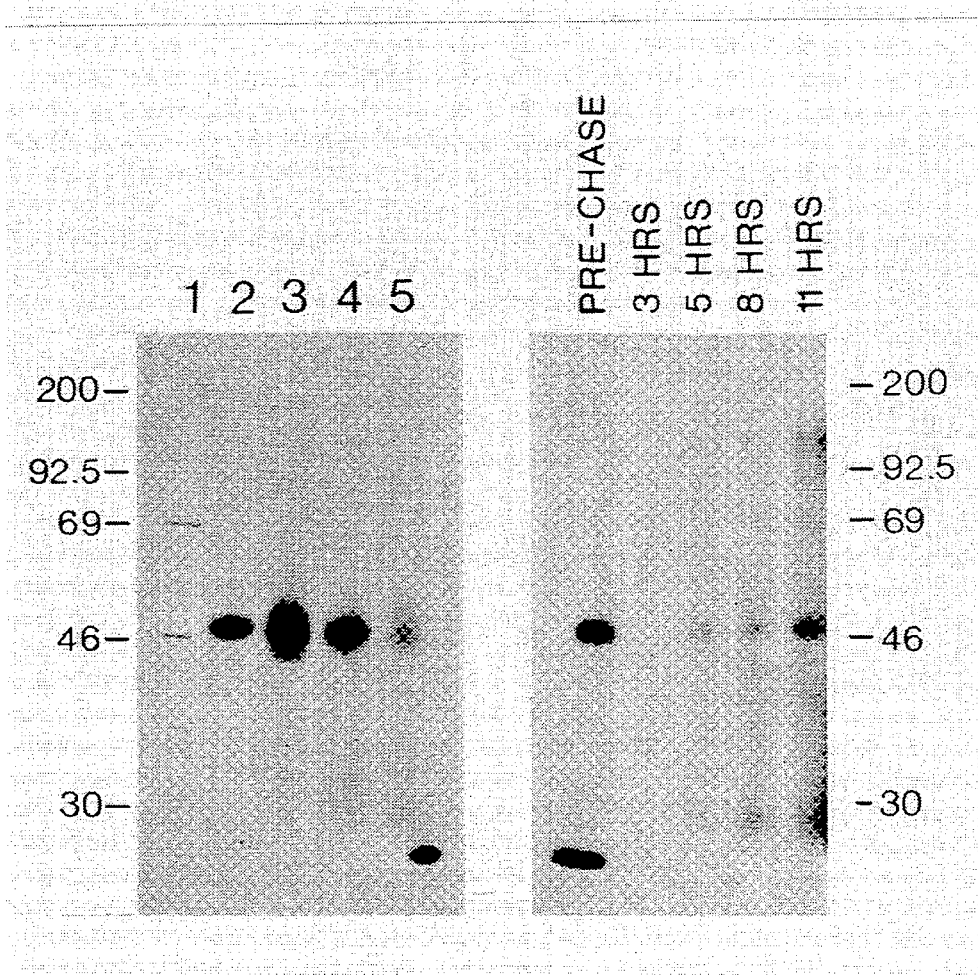

A band of 47 Kd appears in all samples examined, but the relative intensity shows that when the incubation medium is substituted with fresh, unlabelled medium, the presynthesized labelled pro-u-PA is secreted and accumulated (see FIG. 6, left panel). The experiment shows that pro-u-PA is first phosphorylated and then secreted.

Example 7

Time Course of Accumulation
Method
Step 1: Five 6 cm plates of A431 cells were starved and labelled as described in Example 1. After an overnight incubation, the medium was substituted with 0.75 ml of phosphate-containing and serum-free DMEM and each plate incubated for a different time (3 hours, 5 hours, 8 hours, 11 hours, and 24 hours).

Step 2: After the incubation, each 0.75 ml portion was immunoprecipitated and analyzed as described in Example 1.

Results

The pro-u-PA band is barely visible at 3 hours of incubation and its intensity increases with time, showing that it gets accumulated into the medium (see FIG. 6, right panel).

Example 8

Receptor-Bound pro-u-PA is Phosphorylated

A method has been described (Stoppelli et al., 1986) to selectively remove urokinase or pro-u-PA bound to the receptor. Such a procedure was used to determine whether receptor-bound pro-u-PA is also phosphorylated.
Method
Step 1: Ten 15 cm tissue culture dishes of 80% confluent A431 cells were starved for phosphate and labelled as described in Example 1. In parallel, other dishes were starved for methionine and labelled with $^{35}$S-methionine.

Step 2: The labelled medium was removed; the cells were washed two times with PBS and then 3 ml of acid buffer (50 mM glycine, 100 mM NaCl, pH 2.5) were added to remove the pro-u-PA molecules from the receptor.

Step 3: Three samples of i ml each of acid wash were preincubated with glycine-blocked agarose for 1 hour at room temperature to eliminate possible non-specific binding during the immunoprecipitation procedure.

Step 3: The samples were centrifuged in a Microfuge and the supernatants subjected to immunoprecipitation with 5B4 antibody and to SDS-PAGE as described in Example 1.

Results

Figure 7:
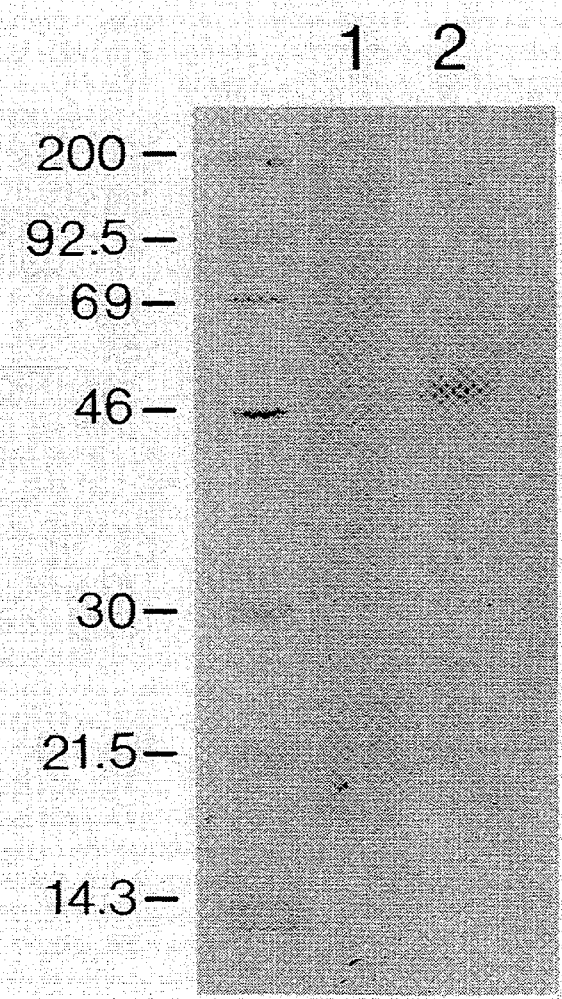

A band corresponding to a molecular weight of 45 Kd is observed. This band is seen both in the $^{32}$P (and in the $^{35}$S labelled) immunoprecipitates from the acid wash (see FIG. 7). Thus, acid wash contains phosphorylated pro-u-PA.

Example 9

Is the Urokinase Receptor Involved in the pro-u-PA Phosphorylation Process?

It is known that many interactions between growth factors and growth factor receptors are accompanied by phosphorylation reactions; some receptors are protein kinases themselves (Hunter, 1987).

The urokinase receptor might mediate a similar response when interacting with endogenously produced pro-u-PA. The cells were labelled under conditions that did not allow the secreted pro-u-PA to bind to the receptor, i.e. in the presence of excess antagonist synthetic peptide [u-PA(12–32)ala19] (Appella et al., 1987).
Method The synthetic peptide [u-PA(12–32)ala19] has an amino acid sequence corresponding to residues 12–32 of the human pro-u-PA. This peptide competes with pro-u-PA for the binding to the urokinase receptor (Appella et al., 1987).

The following procedure was used:

Step 1: Two 10 cm tissue culture dishes of 80% confluent A431 cells were starved for phosphate overnight.

Step 2: The medium was removed and the cells were washed two times with PBS and then with 2 ml of an acid buffer (50 mM glycine, 100 mM NaCl, pH 2.5) for 5 minutes to remove the surface-bound urokinase. The cells were then quickly neutralized by adding 0.5 ml of 0.5M Hepes, pH 7.0.

Step 3: 2 ml of phosphate-free and serum-free medium were added to both plates, one of the two containing the peptide at a final concentration of 100 $\mu$M, and incubated at 4° C. for 30 minutes.

Step 4: 600 $\mu$Ci of $^{32}$P-orthophosphate were added. The labelling period was 6 hours and the labelling was carried out at 37° C.

Step 5: The labelled media were removed and 800 $\mu$l portions thereof were immunoprecipitated and analyzed as described in Example 1.

In parallel, two 6 cm dishes of A431 cells were starved for methionine overnight and then subjected to acid washing and neutralized as described in steps 2 and 3. 750 $\mu$l of methionine-free and serum-free medium were added to the cells. In one of the two dishes, the medium contained the peptide [uPA(12–32)ala19] (final concentration=100 $\mu$M). The cells were incubated at 4° C. for 30 minutes and then labelled with 300 $\mu$Ci of $^{35}$S-methionine for 6 hours at 37° C. and washed again with 600 $\mu$l of acid buffer. Samples of 150 $\mu$l of labelled media and of 600 $\mu$l of acid washing were immunoprecipitated as described in Example 1.

Figure 8:
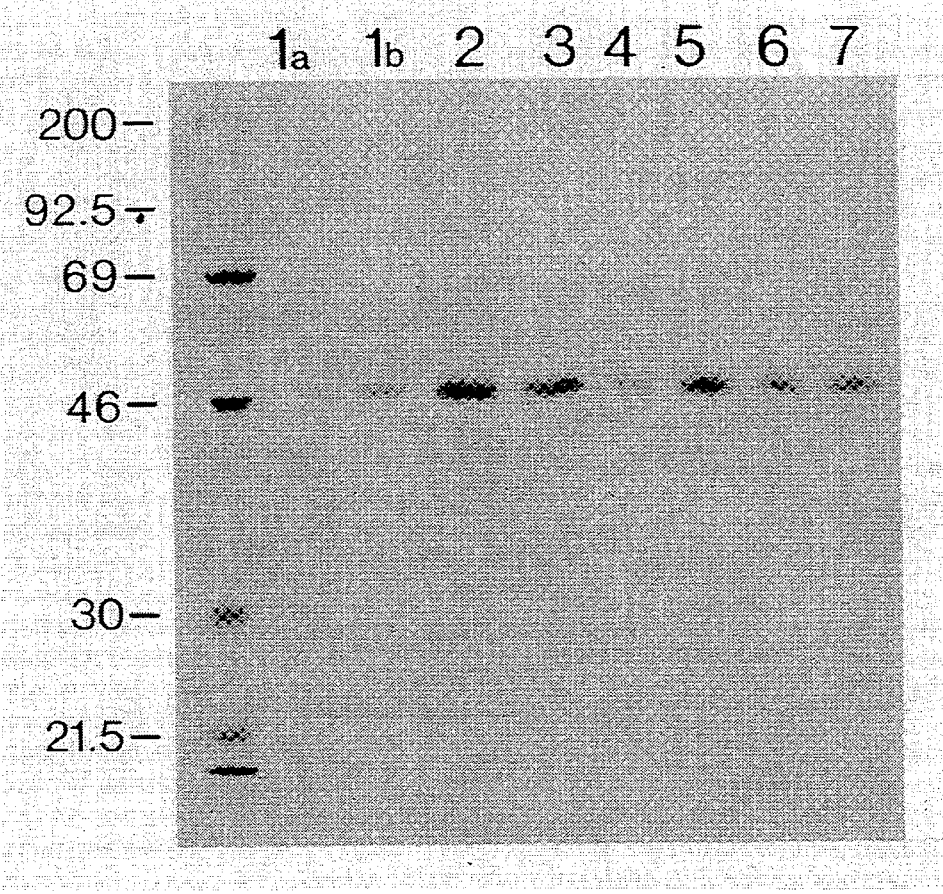

After the immunoprecipitation, the samples labelled with $^{32}$P and those labelled with $^{35}$S-methionine were subjected to SDS-PAGE.
Results 1: The presence of the peptide causes a strong reduction in the amount of pro-u-PA bound to the receptor as seen in the immunoprecipitation of the acid wash from the $^{35}$S labelling (FIG. 8, lanes 1a, 1b).

2: The cells labelled with $^{32}$P-orthophosphate in the presence of the peptide do not show any reduction in the intensity of the 47 Kd band immunoprecipitated from the conditioned medium versus control labelled in the absence of peptide (see FIG. 8, lanes 4–7).

It is therefore concluded that the majority of the phosphorylation is not due to the interaction of pro-u-PA with the urokinase receptor. A protein kinase, located at the interior of the cells, must be responsible for pro-u-PA phosphorylation.

Example 10

Binding of the Phosphorylated pro-u-PA to the PAI-1 Inhibitor

Phosphorylation is a way to regulate the biological activity and/or the enzymatic properties of some proteins (Hargreaves et al., 1986; Sutherland, 1972; Ballou and Fisher, 1986; Cohen, 1988).

Urokinase plasminogen activator is known to be able to interact with three other molecules: the u-PA receptor, the u-PA inhibitor and the substrate, plasminogen. Therefore one may ask whether such activities can be affected by phosphorylation of specific serine residues.

PAI-1 inhibitor is known to bind to the active site of urokinase in a non-reversible way, and to block the enzymatic activity (Andreasen et al., 1986). Taking advantage of the metabolic $^{32}$P-labelling of A431 pro-u-PA which only makes it possible to visualize the phosphorylated molecules, it has been tested whether phosphorylated u-PA is still able to bind to PAI-1 inhibitor.

Step 1: Preparation of the metabolically labelled pro-u-PA: 0.5 ml of $^{35}$S and 2.5 ml of $^{32}$P A431 conditioned medium were prepared and immunoprecipitated as described in Example 1.

Step 2: Plasmin treatment of the labelled pro-u-PA's: TCA-precipitated samples were resuspended in 50 μl of 100 mM Hepes, pH 7.5, and incubated with 2 μg of plasmin/μg of pro-u-PA for 30 minutes at 37° C. 10 μg of aprotinin were then added to block the reaction.

Step 3: Activation of the inhibitor PAI-1 purified as described (Andreasen et al., 1986; Andreasen et al., 1986a): 43 μg/200 μl of PAI-1 inhibitor were supplemented with an equal volume of 8M guanidine and incubated at 37° C. for 1 hour. The sample was then diluted 10 fold with PBS+100 μg/ml BSA and dialyzed using a centricon type tube (AMICON). Dilutions with PBS followed by centrifugation at 3500 rpm for 90 minutes lowered the guanidine concentration to 10 mM final. At the end of the activation-dialysis process, the inhibitor was recovered at the approximate concentration of 43 μg/200 μl.

Step 4: Binding of the $^{32}$P-labelled two-chain u-PA to PAI-1: The right binding conditions were tested with $^{125}$I-urinary urokinase using different ratios between PAI-1 and u-PA. An 8:1 ratio is enough to obtain a complete conversion of the 33K band into the 68K band of the complex u-PA/PAI-1. When analyzed by SDS-polyacrylamide gels under reducing conditions, about 2.5 μg of $^{32}$P pro-u-PA (or 0.5 μg of $^{35}$S pro-u-PA) converted to u-PA were incubated with 20 μg/93 μl (or with 6 μg) of activated and dialyzed PAI-1 for 1 hour at room temperature. At the end of the incubation, the sample was supplemented with Laemmli buffer, boiled and loaded onto a 10% SDS-PAGE.

Results

Figure 9:
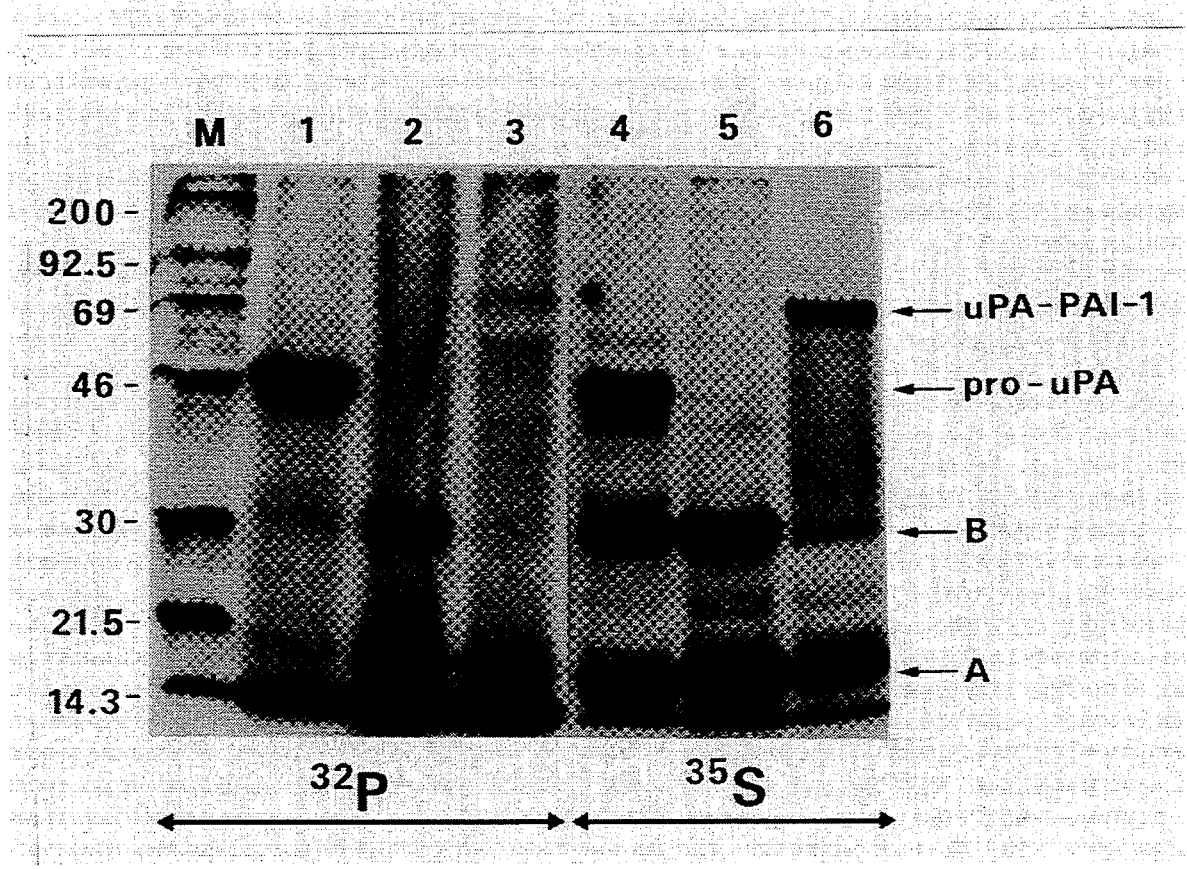

As shown in FIG. 9, while $^{35}$S-labelled plasmin-activated u-PA forms an about 92 Kd complex with PAI-1, the $^{32}$P-labelled plasmin-activated u-PA does not form a complex in visible amounts.

Conclusions

1. Phosphorylated u-PA binds PAI-1 with lower efficiency than $^{35}$S-labelled u-PA. However, both phosphorylated pro-u-PA and pro-u-PA are converted into the two-chain form with the same efficiency. Therefore, phosphorylated u-PA only represents part of the total u-PA.

2. Since only part of the biosynthetic pro-u-PA is phosphorylated, the percentage of phosphorylated pro-u-PA can be increased by in vitro phosphorylation with the appropriate protein kinases.

3. The inability of phosphorylated pro-u-PA may be due to a modification at or near the active site. This does not necessarily imply a decrease or loss of the activity, but makes it possible.

4. The inability of phosphorylated u-PA to bind PAI-1 must result in a longer half-life of soluble and receptor-bound pro-u-PA and u-PA. Therefore, biosynthetic pro-u-PA and u-PA are shielded from the action of the inhibitors.

5. The same conclusions are applicable to the u-PA and pro-u-PA medicaments used in thromboembolic therapy.

Example 11

Identification of the Phosphorylated Sites
Reduction, Carboxymethylation and Tryptic Hydrolysis of $^{32}$P-pro-u-PA 200 μg of purified unlabelled pro-u-PA, mixed with about 30 μg of purified $^{32}$P-labelled pro-u-PA, were TCA-precipitated and redissolved in 25 μl of 6M guanidine-HCl, 0.2% EDTA, 0.2M Tris-HCl pH 8.4, 0.5 μmoles dithiothreitol added, and incubated at 37° C. for 2 hours in an argon atmosphere. Then, a 1.25 fold excess of iodoacetic acid over present —SH groups was added, keeping the pH neutral, and the incubation continued for 30 minutes at room temperature. Reduction and carboxymethylation were stopped by addition of 0.1M dithiothreitol. The protein was then dialyzed against 200 mM ammonium bicarbonate pH 8.0 at 4° C. and then hydrolyzed with trypsin (1 μg/ml in 10 mM $CaCl_2$) for 17 hours at room temperature. The hydrolysis was stopped with 0.1% trifluoroacetic acid and loaded on a HPLC C18 2 mm column at a flow rate of 275 μl/min. with a 0 to 100% gradient of solution B (70% acetonitrile, 0.08% trifluoroacetic acid). Individual fractions were collected, the $^{32}$P radioactivity measured and the radioactive fractions analyzed in an Applied Biosystems protein sequencer model 477A, as recommended by the manufacturer.

$Fe^{3+}$-chelated Chromatographic Separation of Phosphopeptides

Purified pro-u-PA (mixture of $^{32}$P-labelled and unlabelled protein as in the previous paragraph) was carboxymethylated and trypsin-digested as described above. The peptide mixture was brought to pH 3.1 with 0.1M acetic acid, loaded on a $Fe^{3+}$-chelated Sepharose column (Andersson & Porath, 1986;Michel & Bennett, 1987), the column washed with 0.1M acetic acid and eluted stepwise with 10 ml of acetic acid/NaOH buffer pH 5, washed with 10 ml of distilled water, and then eluted with subsequent additions of 10 ml of 1% ammonium acetate pH 7.5, 17 ml of ammonium acetate pH 8.0, and finally with 10 ml of 0.1M potassium phosphate buffer pH 7.4. Several fractions were collected for each step, lyophilized, counted in a scintillation counter and subjected to phosphoamino acid and sequence analysis.

Identification and Measure of Phosphoamino Acids in pro-u-PA Peptides

The cation exchange based amino acid analyzer and the procedures of acid hydrolysis in either liquid or gas phase have been described (Barkholt and Jensen, 1989). Phosphorylated proteins or peptides, however, were hydrolyzed for 2–4 hours only. The hydrolysate was dried and redissolved in 0.1M HCl and 40 μl sample injected. The column had been equilibrated for 30 minutes with an A solvent of pH 1.6 (titrated to pH 1.6 with nitric acid and diluted 4:1 with water) and the phosphorylated amino acids were eluted with this solvent, Ser-P at 4.53 min., Thr-P at 5.23 min., and Tyr-P at 16.6 min.

Tryptic peptides and S-carboxymethylated protein were separated by RP-HPLC on an Applied Biosystem chromatograph, model 130A. The column (220×2.1 mm, RP18, 5 μm) was eluted with a linear gradient from 5-50% acetonitrile in 0.1% trifluoroacetic acid over 50 minutes. Fractions were collected manually.

Results

Figure 10:
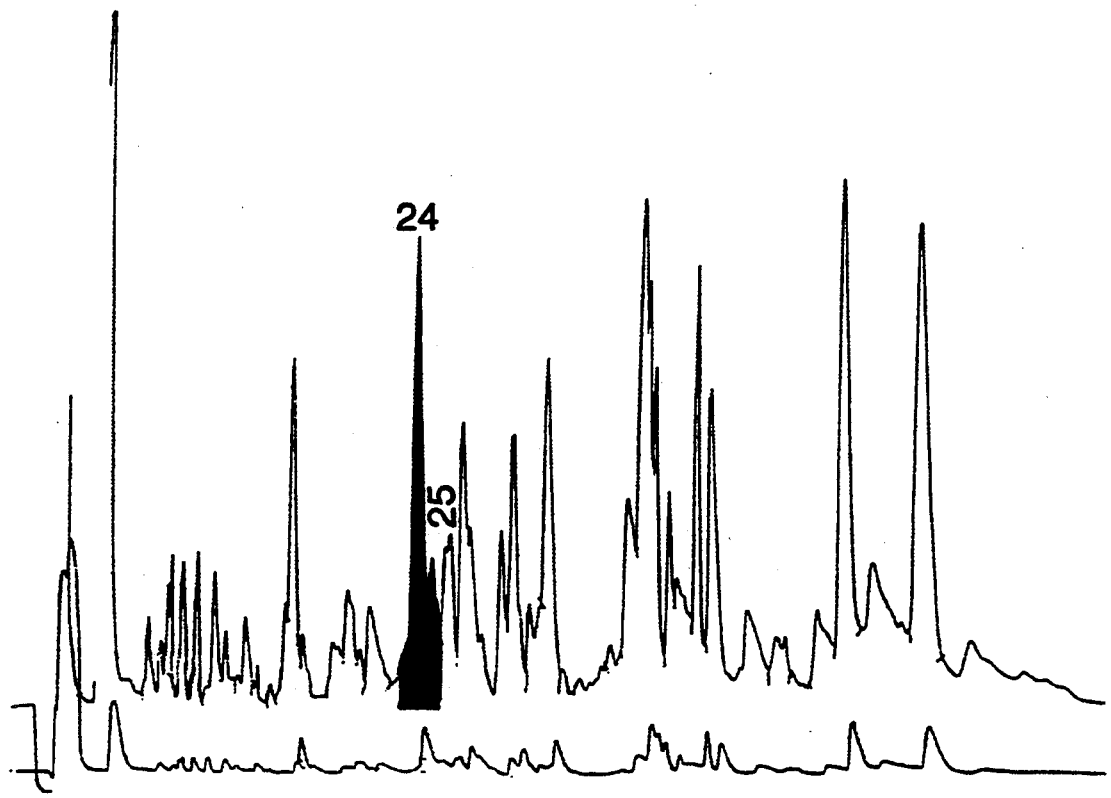
FIG. 10 shows the results of high pressure liquid chromatography (HPLC) separation of peptides produced by tryptic digestion of $^{32}$P-labelled pro-u-PA.

As shown in FIG. 10, HPLC separation mainly yielded two fractions (Nos. 24 and 25) containing significant amounts of radioactivity. Amino acid sequence analysis on fraction 24 yielded three peptides which correspond to the sequences 136-145 (KPSSPPEELK (SEQ I.D. NO:1) using the single letter amino acid code, Eur. J. Biochem. 138, 9-37, 1984), 301-313 (ENSTDYLYPEQLK) (SEQ I.D. NO:2) and 324-338 (ECQQPHYYGSEVTTK) (SEQ I.D. NO:3) of pro-u-PA (see Table 1). Sequence analysis of fraction 25 yielded the same first two 136-145 and 301-313 peptides plus the sequence 37-46 of pro-u-PA (FGGQHCEIDK) (SEQ I.D. NO:4) (Table 1). The latter sequence does not contain any serine residue. The other three, however, do.

Figure 11:
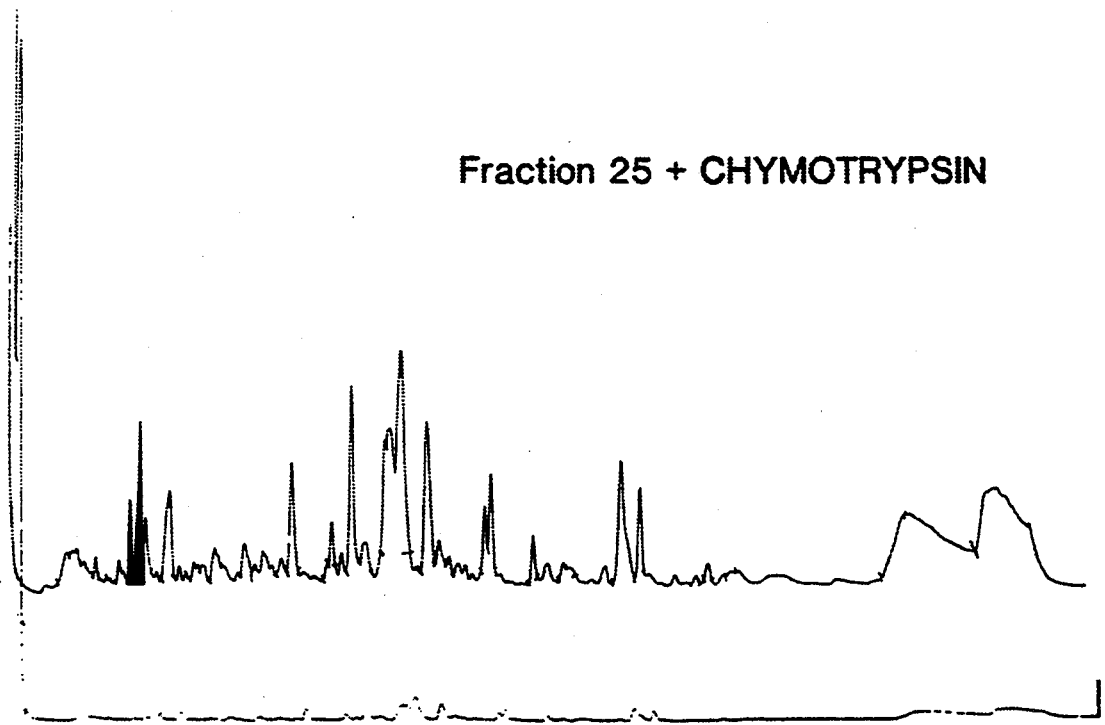
FIG. 11 shows the result of treating pro-u-PA peptide 301–313 with chymotrypsin.
Figure 12:
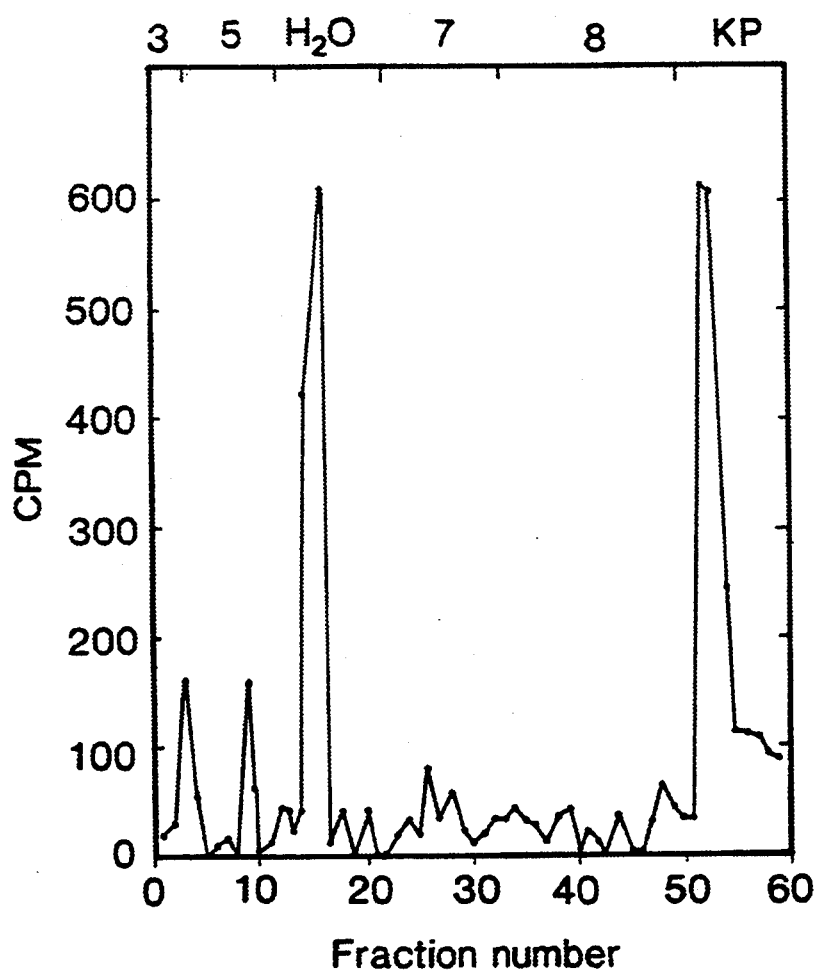
FIG. 12 shows the result of loading a $Fe^{3+}$-chelating Sepharose column with peptides resulting from trypsin digestion of $^{32}$P-labelled pro-u-PA.

Phosphorylation of peptide 301-313 could be proven by treating the peptide with chymotrypsin which shortens it to a ENSTDY (SEQ I.D. NO:5) and therefore changes its HPLC separation (FIG. 11). To identify whether other peptides are phosphorylated, a column of $Fe^{3+}$-chelating Sepharose (Trade Mark) was used to isolate the phosphopeptides of labelled pro-u-PA, as it had previously been done for the photosystem II of spinach (Michel & Bennett, 1987). The column was loaded at pH 3.0, and several washes were tried in which the pH was slowly increased. Only two fractions were found to contain any radioactive material, the water fraction and the potassium phosphate eluate (FIG. 12). Many of the fractions of the $Fe^{3+}$-chelating chromatography were analyzed for phosphoamino acids as well as for normal amino acids.

The results showed complete absence of any phosphoamino acids in all fractions except in the potassium phosphate eluate, fractions 52-55 (Table 2.). In the latter fractions, phosphoserine was the only phosphorylated amino acid, no phosphothreonine or phosphotyrosine could be observed. The estimated yield of phosphoserine (compared to that of lysine and arginine detected under the same conditions) was about 50% assuming one single phosphorylation site per molecule, or 25% assuming two sites per molecule. Thus, phosphoamino acid analysis showed that the material eluted by potassium phosphate did in fact contain phosphoserine residues while the water fraction did not. This may therefore represent free phosphate liberated during the isolation and hydrolysis procedures. The fractions which contained phosphoserine were subjected to amino acid sequence analysis which identified three peptides: a peptide containing the amino terminal sequence of pro-u-PA: SNELHQVP, (SEQ I.D. NO:6) and the two other peptides 136-145 and 301-313 which had previously been identified by HPLC separation (Table 3).

TABLE 1

Amino acid sequence analysis of peptides contained in fractions 24 and 25 of the HPLC column of FIG. 10

| Fraction 24 | Fraction 25 |
| --- | --- |
| KPSSPPEELK (136-145) | KPSSPPEELK (136-145) |
| ENSTDYLYPEQLK (301-313) | ENSTDYLYPEQLK (301-313) |
| ECQQPHYYGSEVTTK (324-338) | FGGQHCEIDK (37-46) |

TABLE 1-continued

Amino acid sequence analysis of peptides contained in fractions 24 and 25 of the HPLC column of FIG. 10

| Fraction 24 | Fraction 25 |
| --- | --- |
|  | (37-46) |

The numbers in parentheses refer to the position of the first and last amino acid in the pro-u-PA sequence (Verde et al., 1984). Each fraction was subjected to amino acid sequence analysis as described above. The three different sequences, indicating three peptides, have been established by comparison with the known sequence of pro-u-PA (Verde et al., 1984).

TABLE 2

Determination of phosphoserine (P-ser) content in the fractions of the $Fe^{3+}$ Sepharose column of FIG. 12. Data expressed in pmoles

| Fraction | P-ser | Lys | Arg |
| --- | --- | --- | --- |
| 9-12 | 0 | 91-100 | 97-110 |
| 13-20 | 0 | 45-70 | 50-76 |
| 26-32 | 0 | 64-113 | 60 |
| 40 | 0 | 141 | 92 |
| 50 | 0 | 137 | 72 |
| 51 | 0 | 108 | 59 |
| 52 | 12 | 271 | 114 |
| 53 | 28 | 291 | 194 |
| 54 | 6 | 78 | 68 |
| 56 | 0 | 78 | 108 |
| 58 | 0 | 66 | 69 |

Fractions 9 to 12, 13 to 20, and 26 to 32 are represented as a group and only the minimum and maximum amounts are shown.

TABLE 3

Amino acid sequence analysis of fractions 52 + 53 of the $Fe^{3+}$ Sepharose column of FIG. 12

SNELHQVP (1-8)
KPSSPPEELK (136-145)
ENSTDYLYPEQLK (301-313)

Numbers in parentheses refer to the position of the first and last amino acid in the pro-u-PA sequence (Verde et al., 1984). The two fractions, 52 and 53, were pooled and subjected to amino acid sequence analysis as described above. Because of the presence of three different sequences, the correct peptide sequence has been identified on the basis of a comparison with the known sequence of pro-u-PA.

Conclusion

Protein-chemical analysis of $^{32}P$-labelled pro-u-PA identified with certainty serine 303 as a site of phosphorylation and strongly suggests serine 138 and/or 139 as a possible second site of phosphorylation. The sequence around serines 138 and 139 suggests that in the latter case, casein kinase II may be the enzyme responsible for phosphorylation. The sequence 1-8 and the sequence 324-338 are probably not phosphorylated; in fact, the first is not labelled during the $^{32}P$-labelling (FIG. 10) and the second is not retained on the $Fe^{3+}$ Sepharose column. It is concluded that pro-u-PA synthesized by A431 cells is phosphorylated at the sites ser138 and ser139, and at ser303.

Example 12

Chromatographic Separation of Phosphorylated and Non-phosphorylated pro-u-PA

A necessary step in analyzing the function of pro-u-PA phosphorylation is the separation of the phosphorylated and non-phosphorylated forms. This allows the analysis of the properties of the phosphorylated and non-phosphorylated enzyme, at both functional and molecular level, and also allows a technique to be set up which can find ways for conversion between the two forms by phosphorylating or dephosphorylating the enzyme.

Materials and Methods

Pro-u-PA was labelled with $^{35}S$ and $^{32}P$ in PMA-treated A431 cells and purified as described in Example 3.

$Fe^{3+}$-chelated Sepharose Batch Chromatography 5 ml of $^{35}S$ and $^{32}P$ conditioned medium of PMA-treated A431 cells were adjusted to pH 3.0 with acetic acid and incubated with 1 ml of $Fe^{3+}$-chelated Sepharose (Pharmacia), prepared as suggested (Michel & Bennett, 1987) as a 1:1 vol:vol suspension in 0.1M acetic acid pH 3.0, presaturated with 2 mg/ml bovine serum albumin. After 45 minutes of incubation at room temperature, the sample was centrifuged and the supernatant removed. The remaining pellet was then supplemented with 0.5M sodium acetate pH 3, incubated at room temperature for 15 minutes, and centrifuged to collect the pH 3 eluted material.

This procedure was repeated with the same buffer at pH 4, 5, 5.5, 6, 6.5, with 1% ammonium acetate buffer pH 7 and 8, and with 200 mM potassium phosphate buffer pH 8.0 containing 0.5M NaCl. Finally, the column was washed with 0.1M EDTA/0.05M Tris-HCl buffer pH 7.5, 0.5M NaCl. Each supernatant was supplemented with potassium phosphate buffer and immunoprecipitated with the 5B4 monoclonal antibody as described in Example 3. The immunoprecipitates were analyzed by 12.5% polyacrylamide gel electrophoresis in SDS (Laemmli, 1970).

Results

Separation of phosphorylated from non-phosphorylated pro-u-PA. The results of the batch elution from $Fe^{3+}$-chelated Sepharose are shown in FIG. 13. The $^{35}S$-pro-u-PA was found distributed throughout the various fractions between pH 5 and 8. Elution with potassium phosphate (KP), however, liberated a substantial amount of $^{32}P$-labelled pro-u-PA which can be estimated to be about 50–60% of the total. In the case of the $^{32}P$-labelled pro-u-PA, however, little or no material was eluted between pH 3 and 8. Most of it sticks to the column and is eluted by the potassium phosphate. Thus, the procedure separates the phosphorylated form of pro-u-PA. Moreover, the separation worked not only for pro-u-PA, but also for two-chain u-PA. Fractions (from the loaded material to the potassium phosphate elution) of both $^{35}S$ and $^{32}P$-labelled material, in addition to the 45 kD band of pro-u-PA, also display the A and B chains of two-chain u-PA, separated from pro-u-PA since the electrophoresis is carried out under reducing conditions.

Conclusions

On the basis of the experiment shown in FIG. 13, batchwise elution of $Fe^{3+}$-Sepharose can be used to separate phosphorylated from non-phosphorylated pro-u-PA and u-PA. Possibly, this procedure can even be improved using a column elution.

Example 13

Catalytic Activity and Sensitivity to PAI-1 of Phosphorylated Pro-urokinase (pro-u-PA)

In order to analyze the specific features of the phosphorylated and non-phosphorylated pro-u-PA, it was necessary first to separate the two forms. To this end, $Fe^{3+}$-chelating chromatography was used. The separated forms were then tested for PAI-1 binding and for the specific catalytic activity.

Materials and Methods

Unlabelled pro-u-PA was prepared and purified from human A431 cells hyperproducing pro-u-PA in the presence of 100 ng/ml PMA (Stoppelli et al., 1986). Under these conditions, A431 cells produce at least 10 fold more pro-u-PA than untreated A431 cells.

Separation of Phosphorylated and Non-phosphorylated pro-u-PA/u-PA

PMA-treated A431 cells were labelled with $^{35}S$-L-methionine as described before, and the labelled pro-u-PA purified as described in Example 3. The phosphorylated and non-phosphorylated pro-u-PA was separated as described in Example 11. Individual fractions were pooled as described in Example 11 and equivalent amounts of pro-u-PA/u-PA mixtures analyzed for PAI-1 complex formation. The low level labelling with $^{35}S$-L-methionine allows quantitation of each sample.

PAI-1/u-PA Complex Formation

The interaction of u-PA with PAI-1 results in the formation of a covalent, sodium dodecyl sulphate (SDS)-resistant complex (Andreasen, Nielsen et al., 1986). PAI-1 only interacts with active two-chain u-PA and not with the single-chain pro-u-PA. Therefore, since the amount of two-chain u-PA in the purified pro-u-PA material was high enough, this was used without previous activation with plasmin. Complex formation was carried out on guanidine-HCl reactivated PAI-1 as previously described (Cubellis et al., 1989).

Determination of the Enzymatic Activity of pro-u-PA/u-PA

The enzymatic activity was determined without prior activation of single-chain pro-u-PA with plasmin since the plasmin contaminant of plasminogen preparations was sufficient to ensure full activation of pro-u-PA to two-chain u-PA (not shown). The activity was measured in 40 $\mu$M Tris-HCl pH 7.5, in the presence of 88 $\mu$g/ml bovine plasminogen and 0.17 mM S-2390 plasmin substrate (Kabi Vitrum, Sweden). Samples were incubated for different periods of time at room temperature, and the colour development was followed with the time at 450 nm. The values obtained were subtracted of a blank value obtained in the absence of added enzyme. The values are expressed as the OD at 450 nm developed in 20 minutes.

Results

PAI-1 Sensitivity of Phosphorylated pro-u-PA/u-PA

To assay the PAI-1 sensitivity of the phosphorylated and non-phosphorylated u-PA, the eluates of the $^{35}S$-pro-u-PA $Fe^{3+}$-chelating Sepharose column (see FIG. 13) were pooled in three groups: pool A (pH 3–5.5), pool B (pH 6–6.5) and the potassium phosphate eluate (KP). Aliquots of each pool along with the total purified pro-u-PA sample applied to the $Fe^{3+}$ Sepharose, containing the same number of $^{35}S$ radioactivity, were incubated, with PAI-1 at different PAI-1 to u-PA ratios (from 0.2:1 to 10:1) and then analyzed by SDS-PAGE and fluorography. Each pool contained the same ratio of single-chain pro-u-PA to two-chain u-PA. Formation of a PAI-1/u-PA complex can be visualized by the formation of an about 90 kD band. As shown in FIG. 14, the band corresponding to the PAI-1/u-PA complex is formed in total pro-u-PA/u-PA pool, in pools A and B, but not in the KP eluate. Therefore, the material eluted by potassium phosphate, despite containing equivalent amounts of two-chain u-PA, reacts poorly with PAI-1 when compared with the other samples. Thus, phosphorylation interferes with binding of u-PA to PAI-1.

Determination of the Activity of Phosphorylated pro-u-PA/u-PA

Aliquots of the fractions obtained with the batchwise elution of $Fe^{3+}$-Sepharose containing the same number of $^{35}S$ counts were assayed for enzymatic activity in the presence of plasmin with a plasmin-specific substrate S-2390. The results are reported in Table 4. The KP fraction (i.e. that eluted with potassium phosphate buffer and representing the phosphorylated pro-u-PA/u-PA) has enzymatic activity comparable to that of the input material, i.e. the pro-u-PA/u-PA isolated from A431 cells. With respect to the presumably non-phosphorylated material (pools A and B), phosphorylated pro-u-PA/u-PA is 20-30% less active. When compared to an international urokinase standard, the KP pool has a specific activity of about 85,000 IU/mg.

TABLE 4

| Enzymatic activity of the pro-u-PA/u-PA fractions separated by batch elution with $Fe^{3+}$-Sepharose | |
|---|---|
| Fraction[a] | Activity[b] |
| Total | 0.44 |
| Pool A | 0.50 |
| Pool B | 0.55 |
| KP | 0.40 |

[a]The fractions used are the same as for the experiment shown in FIG. 14 and are labelled in the same way.
[b]The activity of u-PA is expressed in the OD450 nm developed in 20 minutes of incubation at room temperature, subtracted of a blank value in which no enzyme was added. 5 µl aliquots of each fraction, corresponding to approximately identical values of $^{35}S$ radioactivity, were used in each case.

Conclusions

The data clearly demonstrate that phosphorylated pro-u-PA/u-PA is about as active as the enzyme isolated from A431 cells. However, it is refractory to the specific inhibitor PAI-1. The differential sensitivity to PAI-1 is at least 10 fold lower in the case of phosphorylated u-PA. Phosphorylated u-PA or pro-u-PA therefore represent a therapeutical substitute of common pro-u-PA or u-PA and should allow a decrease in the active dose of at least 10 fold.

Example 14

In Vitro Phosphorylation of pro-u-PA Peptides

A peptide was synthesized that mimic the sequence of pro-u-PA surrounding the phosphoserine residues 138 and 139 identified in Example 11, and its ability to act as a substrate for casein kinase II was tested.

Materials and Methods

Peptides were synthesized with an automatic solid-phase peptide synthesizer (type 430A, Applied Biosystems) and purified by reverse phase HPLC on a NOVAPAK C-18 column using a Waters 501 apparatus. The peptides were lyophilized and dissolved in 0.1M MES pH 6.4, 2 mM EGTA, 5 mM $MgCl_2$. Casein kinase II was purified from rat brain and assayed as described (Maggio et al., 1981).

Kinase assays were performed in a final volume of 0.1 ml containing 100 µM peptides and 10 µM ATP containing 0.5 µCi [gamma-$^{32}P$-ATP]. The samples were incubated at 30° C. and the reactions terminated by the addition of 1M HCl. The samples were then heated for 5 minutes in a boiling water bath and an equal volume of 0.1% trifluoroacetic acid was added. In other cases, the reactions were terminated by adding 30% acetic acid and the samples treated as described (Egan et al., 1988). The samples were loaded onto a reverse phase HPLC column (NOVAPAK C-18) and fractionated using different 0-100% acetonitrile gradients with a flow rate of 0.5 ml/min. Fractions (0.5 ml) were collected and the associated radioactivity determined by liquid scintillation counting (Cerenkov radiation). In some experiments, non-incorporated radioactive ATP and peptides were separated on a Dowex AG 1-X8 column (0.6 ml 20-50 mesh plus 0.2 ml 200-400 mesh, equilibrated with 30% acetic acid).

Results pro-u-PA peptide 133-143 and an irrelevant peptide ITKFGEQSTDY (SEQ I.D. NO:7) were tested. The results are reported in Table 5. These show that peptide pro-u-PA 133-143 is a good substrate for casein kinase II. FIG. 15 shows the HPLC separation of the phosphopeptide from the non-incorporated radioactivity.

TABLE 5

| Phosphorylation of pro-u-PA peptide 133-143 | | | |
|---|---|---|---|
| | cpm $^{32}P$-ATP incorporated | | |
| Protein kinase | CTR | PEP1 | PEP2 |
| Casein kinase II | 4000 | 48000 | 25000 |

CTR = incorporation in the absence of peptide
PEP1 = ITKFGEQSTD (SEQ. I.D. No. 7)
PEP2 = DGKKPSSPPEE (SEQ. I.D. No. 8) (pro-u-PA 133-143)

REFERENCES

Andersson & Porath (1986) Anal. Biochem. 154:250-254

Andreasen PA, Nielsen LS, Kristensen P, Gr$\phi$ndahl-Hansen J, Skriver L, Dan$\phi$ K (1986) Plasminogen activator inhibitor from human fibrosarcoma cells binds urokinase-type plasminogen activator, but not its proenzyme. J Biol Chem 261: 7644-7651

Andreasen PA, Riccio A, Wehnder KG, Douglas R, Sartorio R, Nielsen LS, Oppenheimer C, Blasi F, Dana K (1986a) Plasminogen activator inhibitor type 1. Reactive center and amino-terminal heterogeneity determined by protein and cDNA sequencing. FEBS Letters 209: 213-218

Appella E, Robinson EA, Ullrich SJ, Stoppelli MP, Corti A, Cassani G, Blasi F (1987) The receptor-binding sequence of urokinase. A biological function for the growth-factor module of proteases. J Biol Chem 262: 4437-4440

Ballou LM, Fisher EH (1986) Phosphoprotein phosphatases. The Enzymes 17: 311-361

Barkholt V, Jensn AL (1989) Anal Biochem 177: 318-322

Cohen P (1988) Protein phosphorylation and hormone action, Proc Royal Soc London 234: 115-144

Cubellis MV, Andreasen PA, Ragno P, Mayer M, Dan$\phi$ K, Blasi F (1989) Accessibility of receptor-bound urokinase to type-1 plasminogen activator inhibitor. Proc Natl Acad Sci USA 86: 4828-4832

Dalchau R, Kirkley J, Fabre JW (1980) Monoclonal antibody to a human leukocyte-specific membrane glycoprotein probably homologous to the leukocyte-common (L-C) antigen of the rat, Eur. J. Immunol. 10, pp. 737-744

Egan, Chang & Londos (1988) Anal Biochem 175: 552-561

Fabricant et al. (1977) Proc Natl Acad Sci USA 74: 565-569

Harboe and Ingild, Scand. J. Immun. 2 (Suppl. 1), 1973, pp. 161–164.)

Hargreaves AJ, Wandossell F, Avila J (1986) Phosphorylation of tubulin enhances its interaction with membranes. Nature 323: 827–828

Hunter T (1987) Thousand and one kinases. Cell 50: 823–829

Köhler and Milstein, Nature 256, 1975, p. 495

Laemmli UK (1970) Nature 227: 680–685

Maggio, Deave & Pinna (1981) J Biol Chem 251: 11958–11967

Michel & Bennett (1987) FEBS Letters 212: 103–108

Nolli ML et al. (1986) Thrombosis and Haemost. 56: 214–218

Stoppelli MP, Corti A, Soffientini A, Cassani G, Blasi F, Assoian RK (1985) Differentiation-enhanced binding of the amino-terminal fragment of human urokinase plasminogen activator to a specific receptor on U937 monocytes. Proc Natl Acad Sci USA 82: 4939–4943

Stoppelli MP, Tacchetti C, Cubellis MV, Corti A, Hearing VJ, Cassani G, Appella E, Blasi F (1986) Autocrine saturation of pro-urokinase receptors on human A431 cells. Cell 45: 675–684

Stoppelli MP, Verde P, Grimaldi G, Locatelli EK, Blasi F (1986) Increase in u-PA mRNA synthesis in human carcinoma cells is a primary effect of potent tumor promoter PMA. J Cell Biol 102: 1235–1241

Sutherland EW (1972) Studies on the mechanism of hormone action. Science 177: 401–408

Verde et al. (1984) Identification and primary sequence of an unspliced urokinase polyA+ RNA. Proc Natl Acad Sci USA 81, 4727–4731

---

We claim:

1. A process for obtaining phosphorylated u-PA substantially free from unphosphorylated u-PA, which process comprises separating phosphorylated u-PA from a mixture of phosphorylated u-PA and unphosphorylated u-PA.

2. A process for obtaining phosphorylated pro-u-PA substantially free from unphosphorylated pro-u-PA, which process comprises separating phosphorylated pro-u-PA from a mixture of phosphorylated pro-u-PA and unphosphorylated pro-u-PA.

3. A process according to claim 1, which process comprises:
   (i) culturing a human cell line which produces u-PA;
   (ii) isolating the u-PA thus produced; and
   (iii) separating the phosphorylated u-PA from the unphosphorylated u-PA.

4. A process according to claim 2, which process comprises:
   (i) culturing a human cell line which produces pro-u-PA;
   (ii) isolating the pro-u-PA thus produced; and
   (iii) separating the phosphorylated pro-u-PA from the unphosphorylated pro-u-PA.

5. A process for the preparation of phosphorylated u-PA substantially free from unphosphorylated u-PA, which process comprises phosphorylating unphosphorylated u-PA with a phosphorylating enzyme.

6. A process for the preparation of phosphorylated pro-u-PA substantially free from unphosphorylated pro-u-PA, which process comprises phosphorylating unphosphorylated pro-u-PA with a phosphorylating enzyme.

7. A process according to claim 5, wherein a mixture of phosphorylated and unphosphorylated u-PA is treated with the phosphorylating enzyme.

8. A process according to claim 6, wherein a mixture of phosphorylated and unphosphorylated pro-u-PA is treated with the phosphorylating enzyme.

9. A process for the preparation of phosphorylated u-PA which is substantially free from unphosphorylated u-PA, which process comprises treating, with plasmin, phosphorylated pro-u-PA which is substantially free from unphosphorylated pro-u-PA.

10. A process for obtaining pro-u-PA wherein at least one of serine residues 138, 139 or 303 is phosphorylated and which is substantially free from unphosphorylated pro-u-PA, which process comprises separating said phosphorylated pro-u-PA from a mixture of phosphorylated pro-u-PA and unphosphorylated pro-u-PA.

11. A process for obtaining u-PA wherein at least one of serine residues 138, 139 or 303 is phosphorylated and which is substantially free from unphosphorylated u-PA, which process comprises separating said phosphorylated u-PA from a mixture of phosphorylated u-PA and unphosphorylated u-PA.

12. A process according to claim 10, which process comprises:
   (i) culturing a human cell line which produces pro-u-PA wherein at least one of serine residues 138, 139 or 303 is phosphorylated;
   (ii) isolating the pro-u-PA thus produced; and
   (iii) separating the phosphorylated pro-u-PA from the unphosphorylated pro-u-PA.

13. A process according to claim 11, which process comprises:
   (i) culturing a human cell line which produces u-PA wherein at least one of serine residues 138, 139 or 303 is phosphorylated;
   (ii) isolating the u-PA thus produced; and
   (iii) separating the phosphorylated u-PA from the unphosphorylated u-PA.

14. A process according to any of claims 1, 2, 10 or 11, wherein the separation is effected by $Fe^{3+}$-chelating chromatography.

15. A process for the preparation of phosphorylated pro-u-PA wherein least one of serine residues 138, 139 or 303 is phosphorylated which process comprises phosphorylating unphosphorylated pro-u-PA with a phosphorylating enzyme such that at least one of serine residues 138, 139 or 303 of the unphosphorylated pro-u-PA is phosphorylated.

16. A process for the preparation of phosphorylated u-PA wherein at least one of serine residues 138, 139 or 303 is phosphorylated which process comprises phosphorylating unphosphorylated u-PA with a phosphorylating enzyme such that at least one of serine residues 138, 139 or 303 of the unphosphorylated u-PA is phosphorylated.

17. A process for the preparation of phosphorylated u-PA wherein at least one of serine residues 138, 139 or 303 is phosphorylated and which u-PA is substantially free from unphosphorylated u-PA, which process comprises treating, with plasmin, phosphorylated pro-u-PA wherein at least one of serine residues 138, 139 or 303 is phosphorylated and which is substantially free from unphosphorylated pro-u-PA.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: N ( v ) FRAGMENT TYPE: internal ( x i ) SEQUENCE DESCRIPTION: SEQ ID NO:1:

```
Lys  Pro  Ser  Ser  Pro  Pro  Glu  Glu  Leu  Lys
1                  5                       10
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i i i ) HYPOTHETICAL: N ( v ) FRAGMENT TYPE: internal ( x i ) SEQUENCE DESCRIPTION: SEQ ID NO:2:

```
Glu  Asn  Ser  Thr  Asp  Tyr  Leu  Tyr  Pro  Glu  Gln  Leu  Lys
1                  5                       10
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: N ( v ) FRAGMENT TYPE: internal ( x i ) SEQUENCE DESCRIPTION: SEQ ID NO:3:

```
Glu  Cys  Gln  Gln  Pro  His  Tyr  Tyr  Gly  Ser  Glu  Val  Thr  Thr  Lys
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: N ( v ) FRAGMENT TYPE: internal ( x i ) SEQUENCE DESCRIPTION: SEQ ID NO:4:

Phe Gly Gly Gln His Cys Glu Ile Asp Lys
    1               5                  10

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: N ( v ) FRAGMENT TYPE: internal ( x i ) SEQUENCE DESCRIPTION: SEQ ID NO:5:

Glu Asn Ser Thr Asp Tyr
    1               5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i i i ) HYPOTHETICAL: N ( v ) FRAGMENT TYPE: N-terminal ( x i ) SEQUENCE DESCRIPTION: SEQ ID NO:6:

Ser Asn Glu Leu His Gln Val Pro
    1               5

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i i i ) HYPOTHETICAL: N ( v ) FRAGMENT TYPE: internal ( x i ) SEQUENCE DESCRIPTION: SEQ ID NO:7:

Ile Thr Lys Phe Gly Glu Gln Ser Thr Asp Tyr
    1               5                  10

( 2 ) INFORMATION FOR SEQ ID NO:8:

( i ) SEQUENCE CHARACTERISTICS:

(A) LENGTH: 11 amino acids
(B) TYPE: amino acid
(D) TOPOLOGY: linear (ii) MOLECULE TYPE: peptide (iii) HYPOTHETICAL: N (v) FRAGMENT TYPE: internal (xi) SEQUENCE DESCRIPTION: SEQ ID NO:8:

```
Asp  Gly  Lys  Lys  Pro  Ser  Ser  Pro  Pro  Glu  Glu
 1              5                        10
```